United States Patent [19]

Krohn et al.

[11] Patent Number: 5,225,763

[45] Date of Patent: Jul. 6, 1993

[54] BATTERY CHARGING CIRCUIT AND METHOD FOR AN AMBULATORY FEEDING PUMP

[75] Inventors: Randall J. Krohn, Ballwin; Denis Y. Yerlikaya, Des Peres, both of Mo.

[73] Assignee: Sherwood Medical Company, St. Louis, Mo.

[21] Appl. No.: 817,012

[22] Filed: Jan. 3, 1992

Related U.S. Application Data

[63] Continuation-in-part of Ser. No. 672,531, Mar. 20, 1991, abandoned.

[51] Int. Cl.$^5$ .............................................. H02J 7/04
[52] U.S. Cl. ........................................ 320/23; 320/20; 320/39
[58] Field of Search .................. 320/2, 22, 23, 24, 20, 320/37, 38, 31, 32, 39, 40

[56] References Cited

U.S. PATENT DOCUMENTS

| | | | |
|---|---|---|---|
| 3,098,188 | 7/1963 | Dawkins | 320/31 |
| 3,603,862 | 9/1971 | Chase et al. | 320/39 |
| 3,890,556 | 6/1975 | Melling et al. | 320/21 |
| 3,936,718 | 2/1976 | Melling et al. | 320/20 |
| 3,938,021 | 2/1976 | Kosmin | 320/40 |
| 4,035,709 | 7/1977 | Seider et al. | 320/23 |
| 4,080,558 | 3/1978 | Sullivan | 320/39 |
| 4,118,661 | 10/1978 | Siekierski et al. | 320/40 |
| 4,134,056 | 1/1979 | Fukui et al. | 320/20 |
| 4,136,310 | 1/1979 | Foster | 320/37 |
| 4,137,493 | 1/1979 | Smith | 320/39 |
| 4,210,854 | 7/1980 | Godard | 320/23 X |
| 4,213,081 | 7/1980 | Taylor | 320/40 |
| 4,223,262 | 9/1980 | Ballman | 320/40 |
| 4,240,022 | 12/1980 | Kilinskis et al. | 320/23 |
| 4,260,943 | 4/1981 | Zaderej et al. | 320/21 |
| 4,354,148 | 10/1982 | Tada et al. | 320/20 |
| 4,387,332 | 6/1983 | Oyamada et al. | 320/15 |
| 4,388,582 | 6/1983 | Saar et al. | 320/20 |
| 4,392,101 | 7/1983 | Saar et al. | 320/20 |
| 4,394,611 | 7/1983 | Fallon et al. | 320/23 X |
| 4,395,672 | 7/1983 | Gassaway | 320/31 |
| 4,396,880 | 8/1983 | Windebank | 320/21 |
| 4,426,612 | 1/1984 | Wicnienski et al. | 320/39 |
| 4,455,523 | 6/1984 | Koenck | 320/43 |
| 4,467,265 | 8/1984 | Hierholzer, Jr. | 320/17 |

(List continued on next page.)

FOREIGN PATENT DOCUMENTS

| | | |
|---|---|---|
| 0763850 | 5/1971 | Belgium . |
| 0124739 | 11/1984 | European Pat. Off. . |
| 2544548 | 4/1977 | Fed. Rep. of Germany . |
| 0294225 | 11/1988 | Japan . |
| 0023731 | 1/1989 | Japan . |
| 8400614 | 2/1984 | PCT Int'l Appl. . |
| 8908940 | 9/1989 | PCT Int'l Appl. . |

OTHER PUBLICATIONS

Zinder, "Fast-Charging Systems for Ni-Cd Batteries", Jan. 15, 1970, pp. 65-67.
General Electric Company, "Nickel-Cadmium Battery Application Handbook", Third Ed. 1986.
General Electric, "Charging Circuit for CADNICA Batteries", date unknown, pp. 9 and 3-8-3-10.
Gates Energy Products, "Charging", date unknown, pp. 53-74.

*Primary Examiner*—Steven L. Stephan
*Assistant Examiner*—Kristine L. Peckman
*Attorney, Agent, or Firm*—Andrew J. Beck; Montgomery W. Smith; Curtis D. Kinghorn

[57] ABSTRACT

A device having a rechargeable power source with an associated battery charger base having a quick charge current output and a trickle charge current output. A control circuit within the device is also provided that monitors if and for how long the device is attached to the base and determines the present capacity of the power source. Based on these signals, the control circuit selects an appropriate charge current output. The control circuit also includes timer circuits and circuits to measure the battery voltage during charging to allow for maximum but safe quick charging to protect the power source from long-term damage.

30 Claims, 16 Drawing Sheets

U.S. PATENT DOCUMENTS

| | | | |
|---|---|---|---|
| 4,468,605 | 8/1984 | Fitzgerald et al. | 320/36 |
| 4,549,127 | 10/1985 | Taylor et al. | 320/21 |
| 4,551,666 | 11/1985 | Wada et al. | 320/20 |
| 4,553,081 | 11/1985 | Koenck | 320/43 |
| 4,583,035 | 4/1986 | Sloan | 320/22 |
| 4,639,655 | 1/1987 | Westhaver et al. | 320/20 X |
| 4,639,656 | 1/1987 | Mukai | 320/22 |
| 4,668,901 | 5/1987 | Furukawa | 320/23 X |
| 4,670,701 | 6/1987 | Sako et al. | 320/2 |
| 4,670,703 | 6/1987 | Williams | 320/22 |
| 4,709,202 | 11/1987 | Koenck et al. | 320/43 |
| 4,710,694 | 12/1987 | Sutphin et al. | 320/24 X |
| 4,716,354 | 12/1987 | Hacker | 320/39 |
| 4,727,306 | 2/1988 | Misak et al. | 320/20 X |
| 4,742,290 | 5/1988 | Sutphin et al. | 320/21 |
| 4,746,854 | 5/1988 | Baker et al. | 320/20 X |
| 4,767,977 | 8/1988 | Fasen et al. | 320/20 |
| 4,806,840 | 2/1989 | Alexander et al. | 320/20 |
| 4,888,544 | 12/1989 | Terry et al. | 320/22 X |
| 4,918,368 | 4/1990 | Baker et al. | 320/40 |
| 4,965,738 | 10/1990 | Bauer et al. | 320/39 |
| 4,992,720 | 2/1991 | Hata | 320/23 |
| 5,013,992 | 5/1991 | Eavenson et al. | 320/31 |
| 5,036,284 | 7/1991 | Cichanski | 324/433 |
| 5,055,763 | 10/1991 | Johnson et al. | 320/15 |
| 5,089,763 | 2/1992 | Van Der Linden et al. | 320/20 |

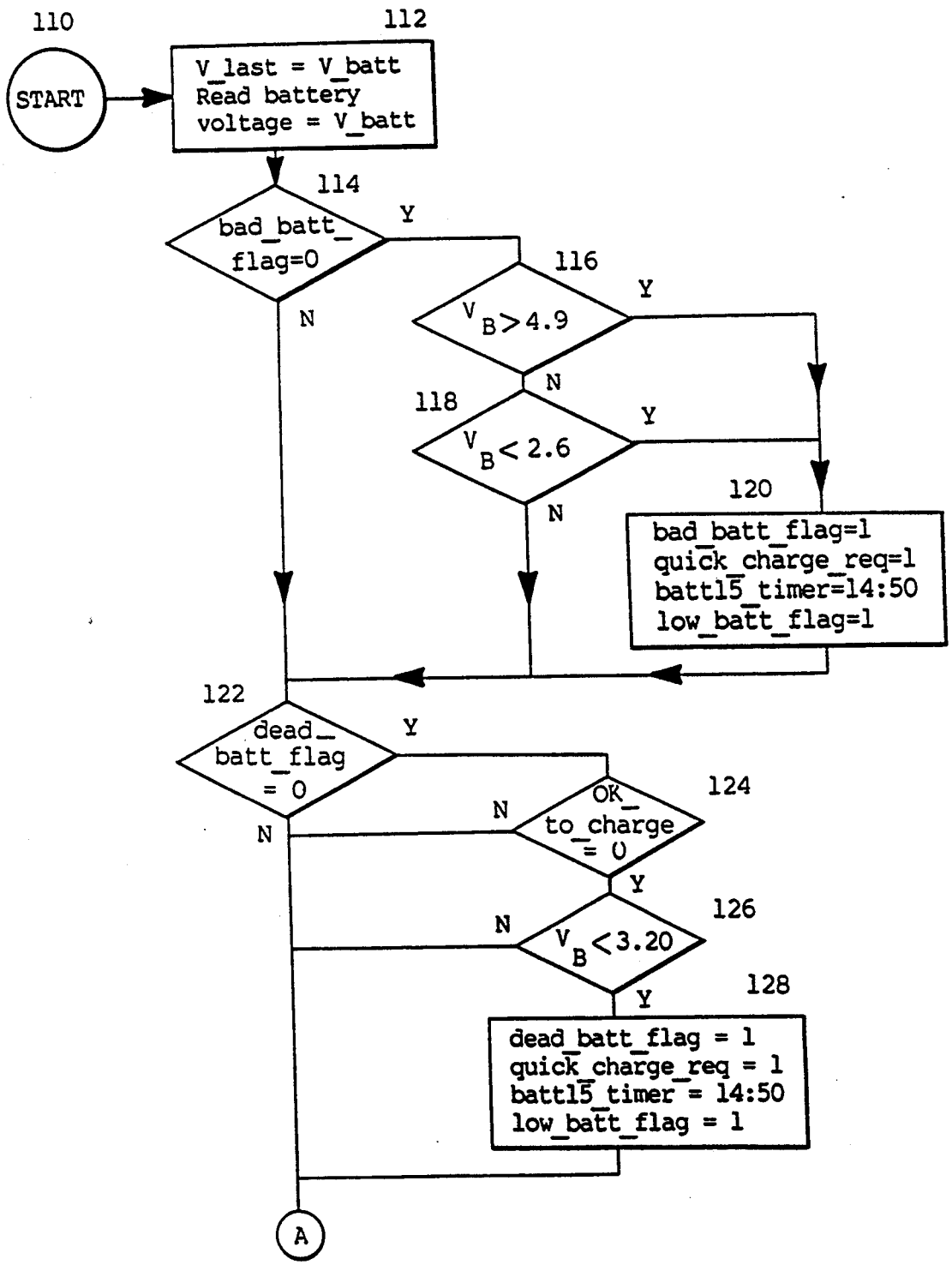
FIG 4A BAD BATT/DEAD BATT DETECTION

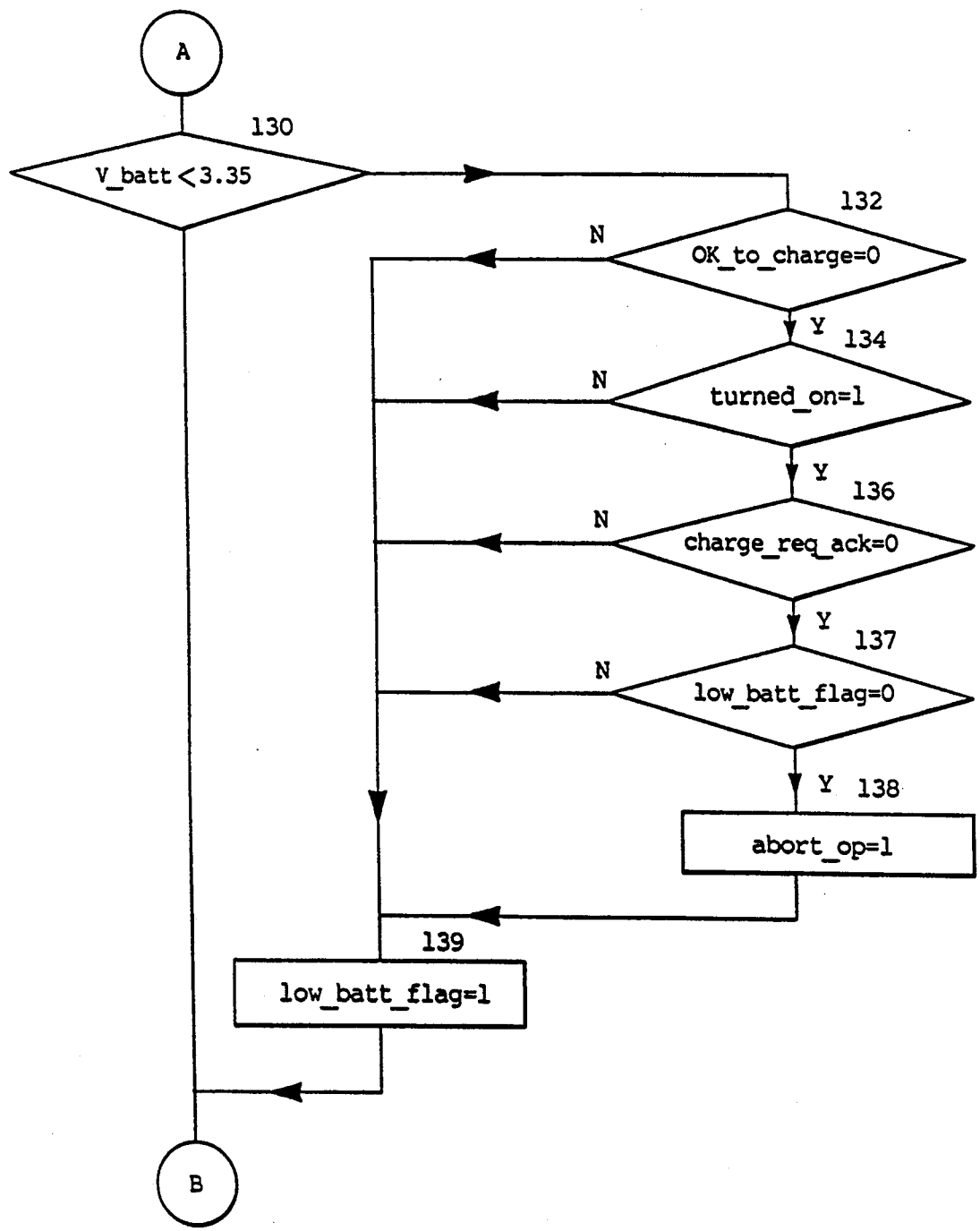
FIG 4B LOW BATT DETECTION

FIG 4Ci BATTERY ERROR GENERATOR/TIMER
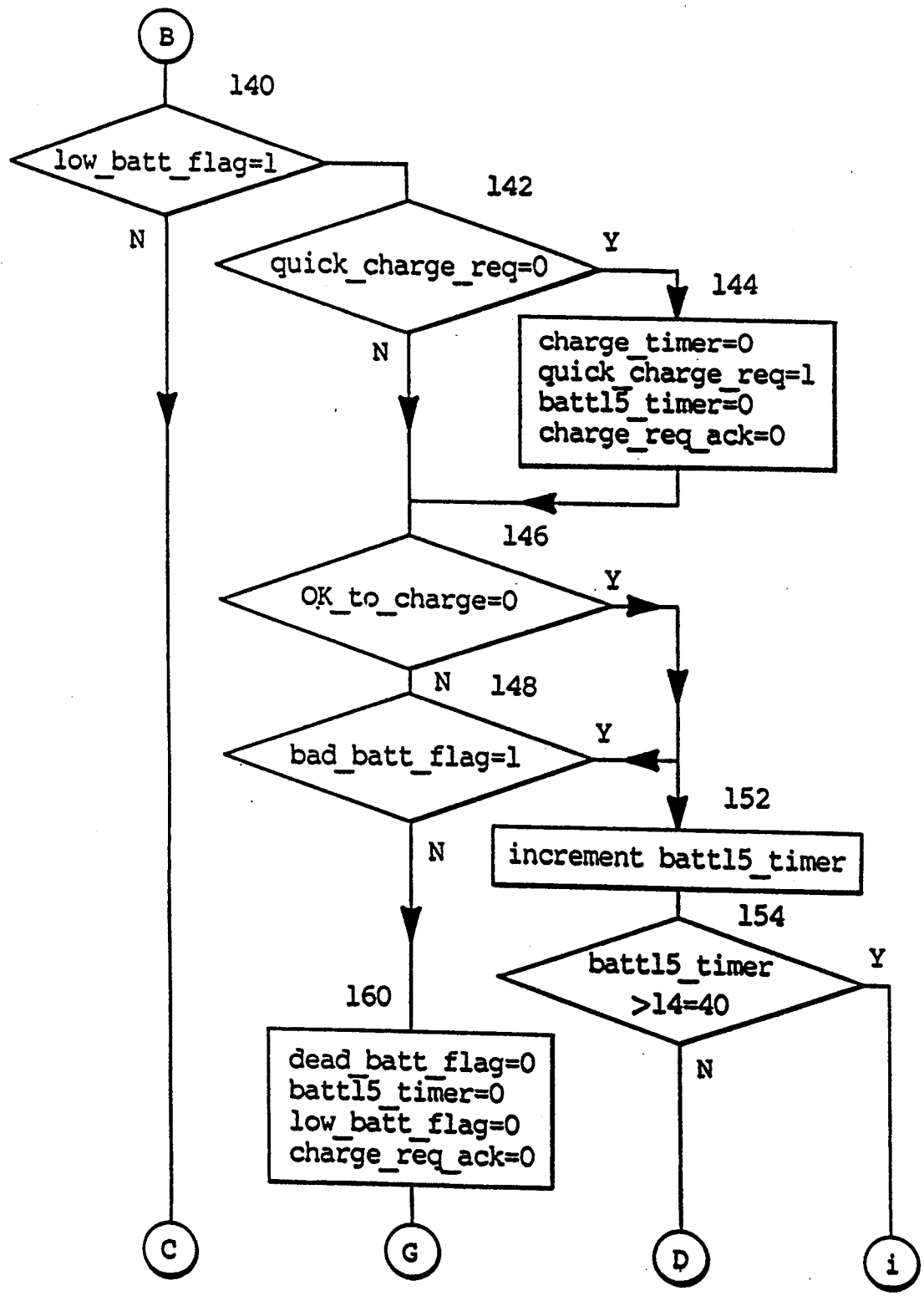

FIG 4Cii BATTERY ERROR GENERATOR/TIMER
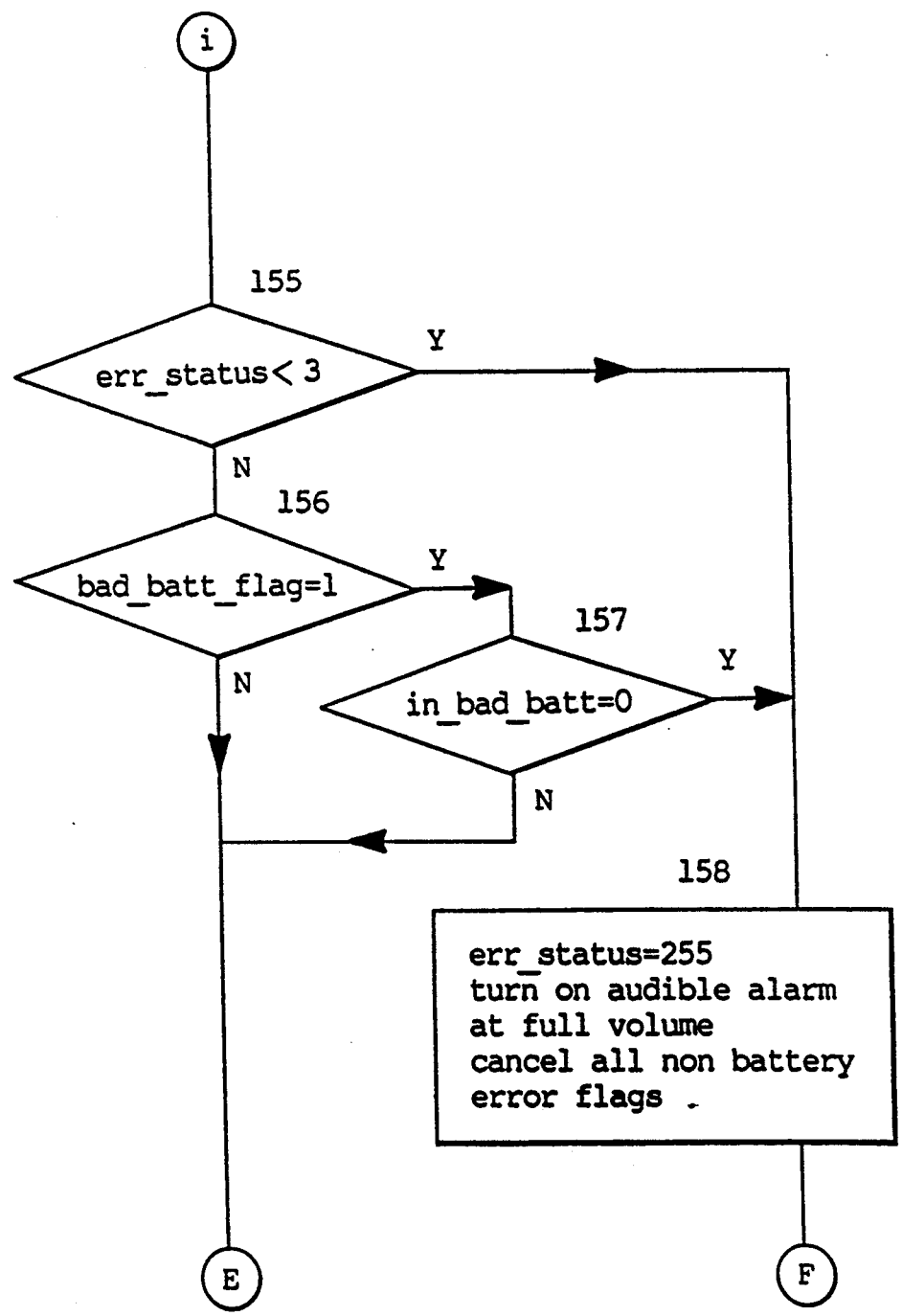

FIG 4D (4C cont'd)
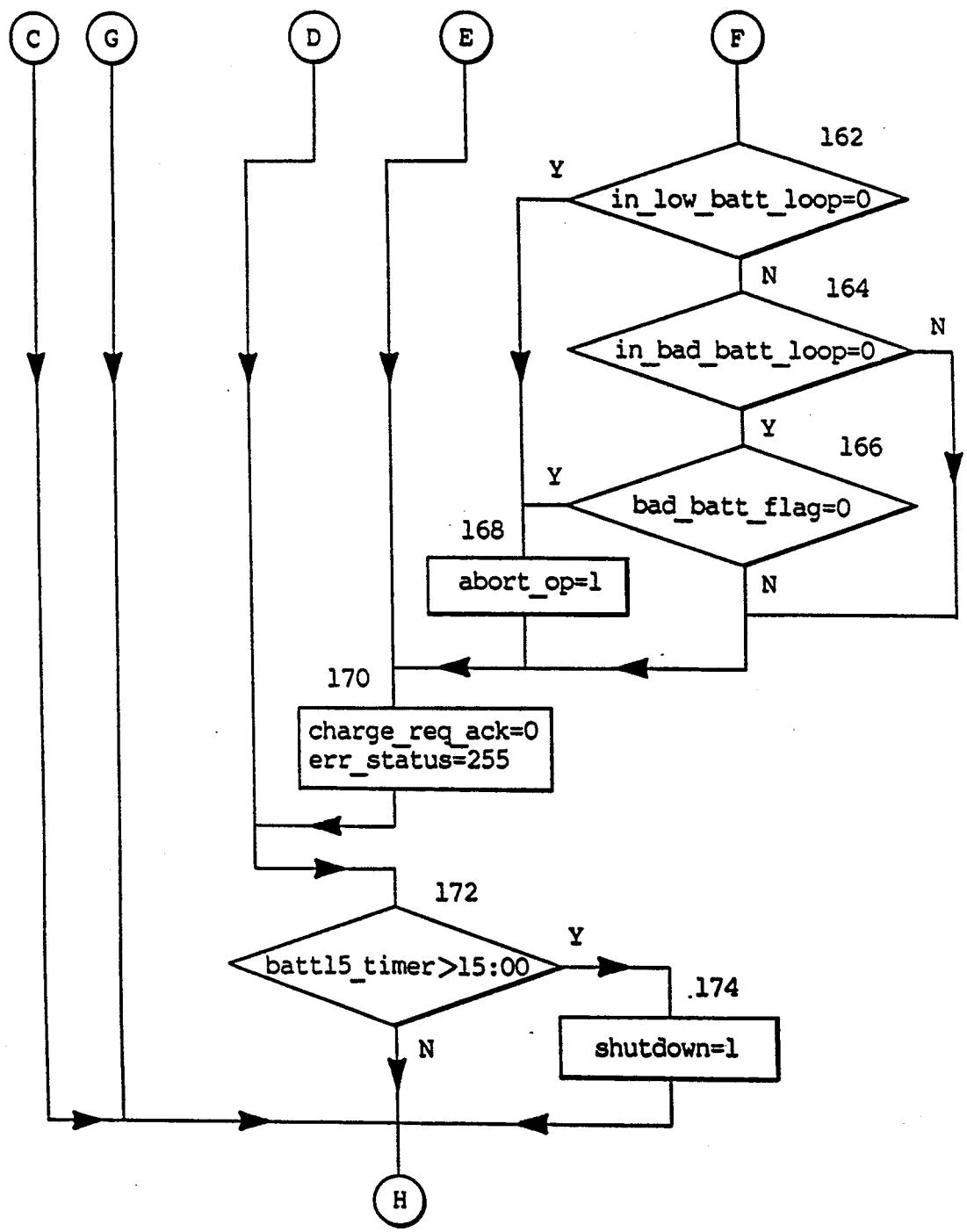

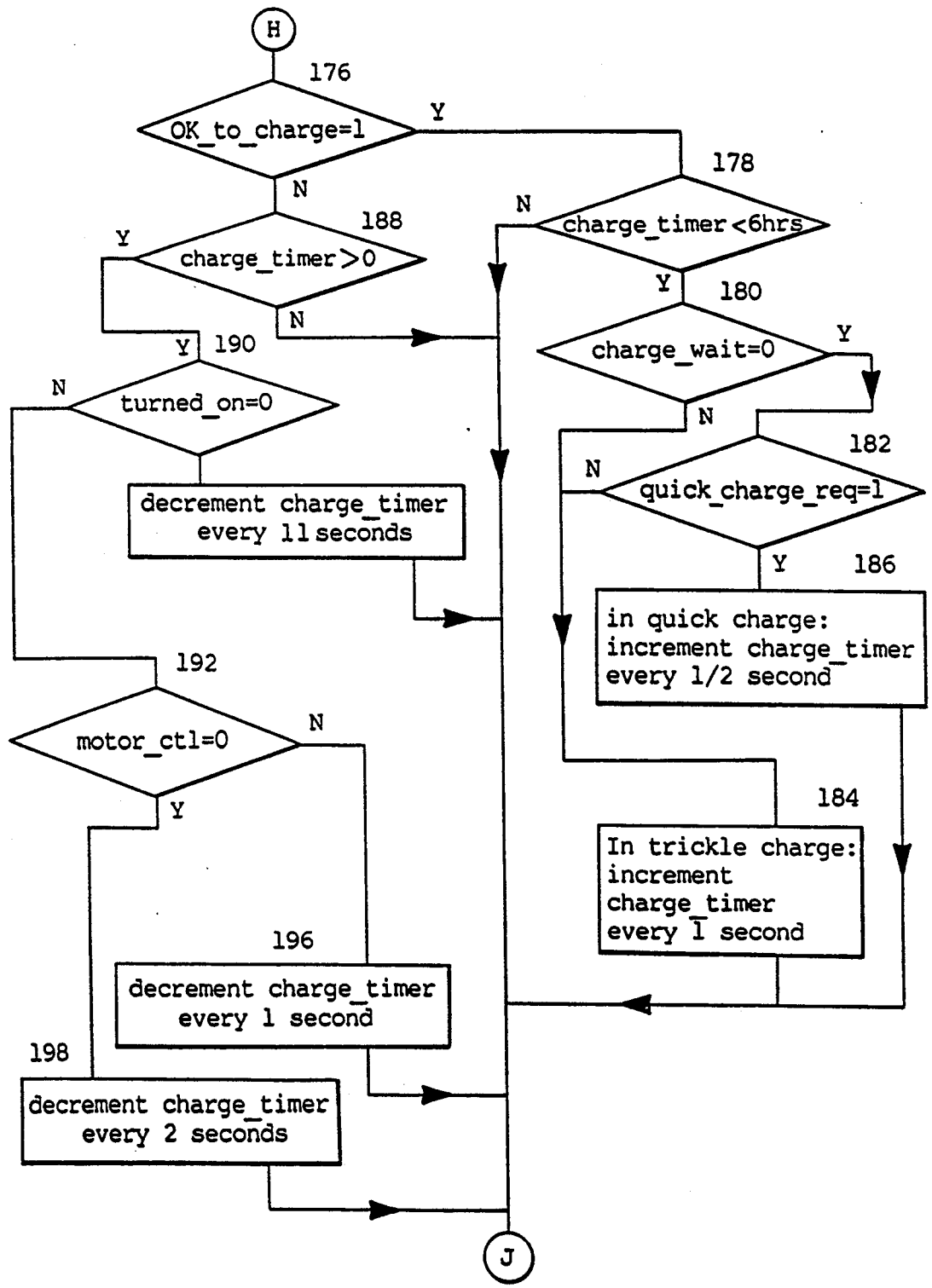
FIG 4E CHARGE COMPENSATION

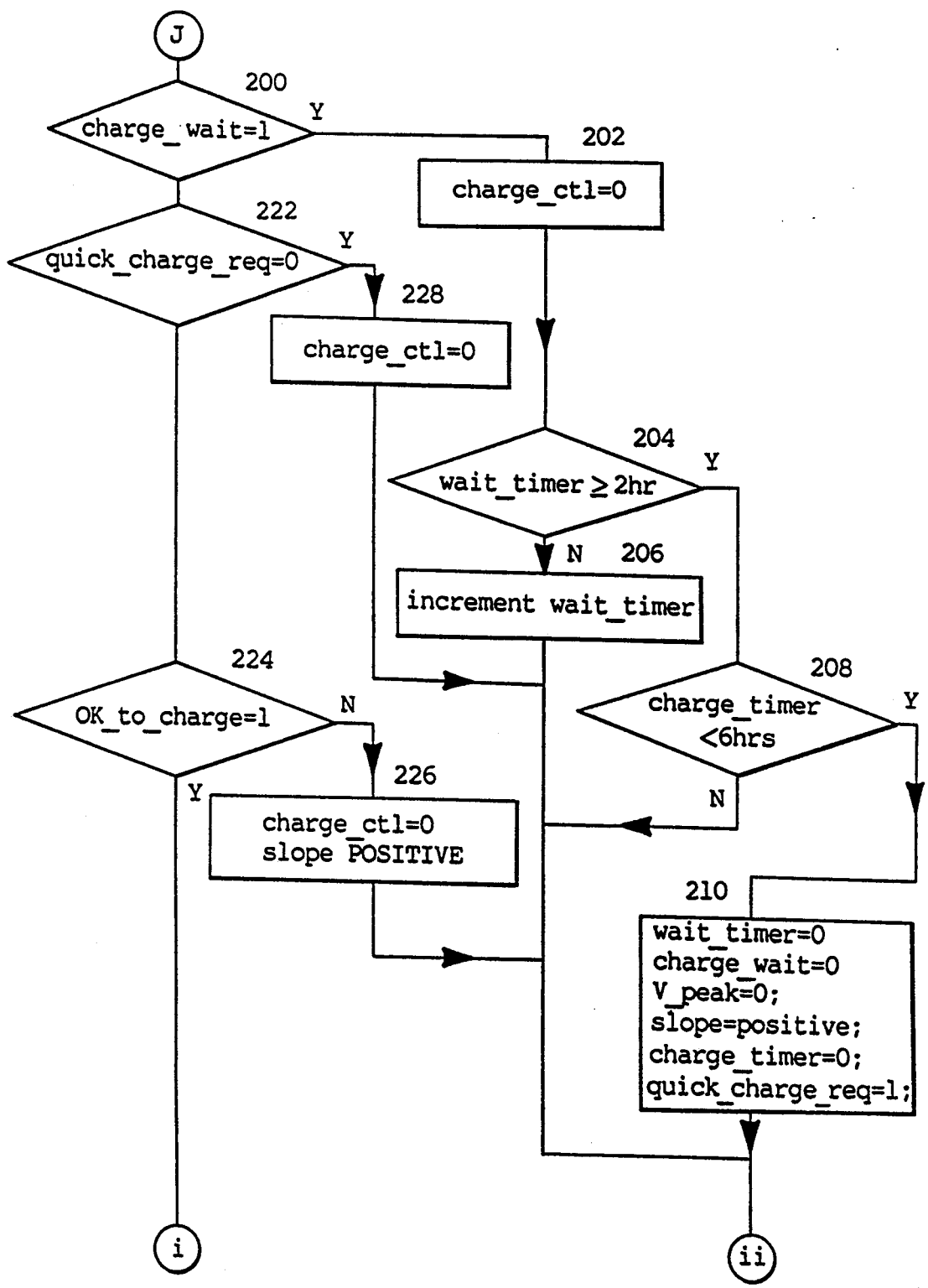
FIG 4Fi CHARGE CONTROL

FIG 4Fii CHARGE CONTROL
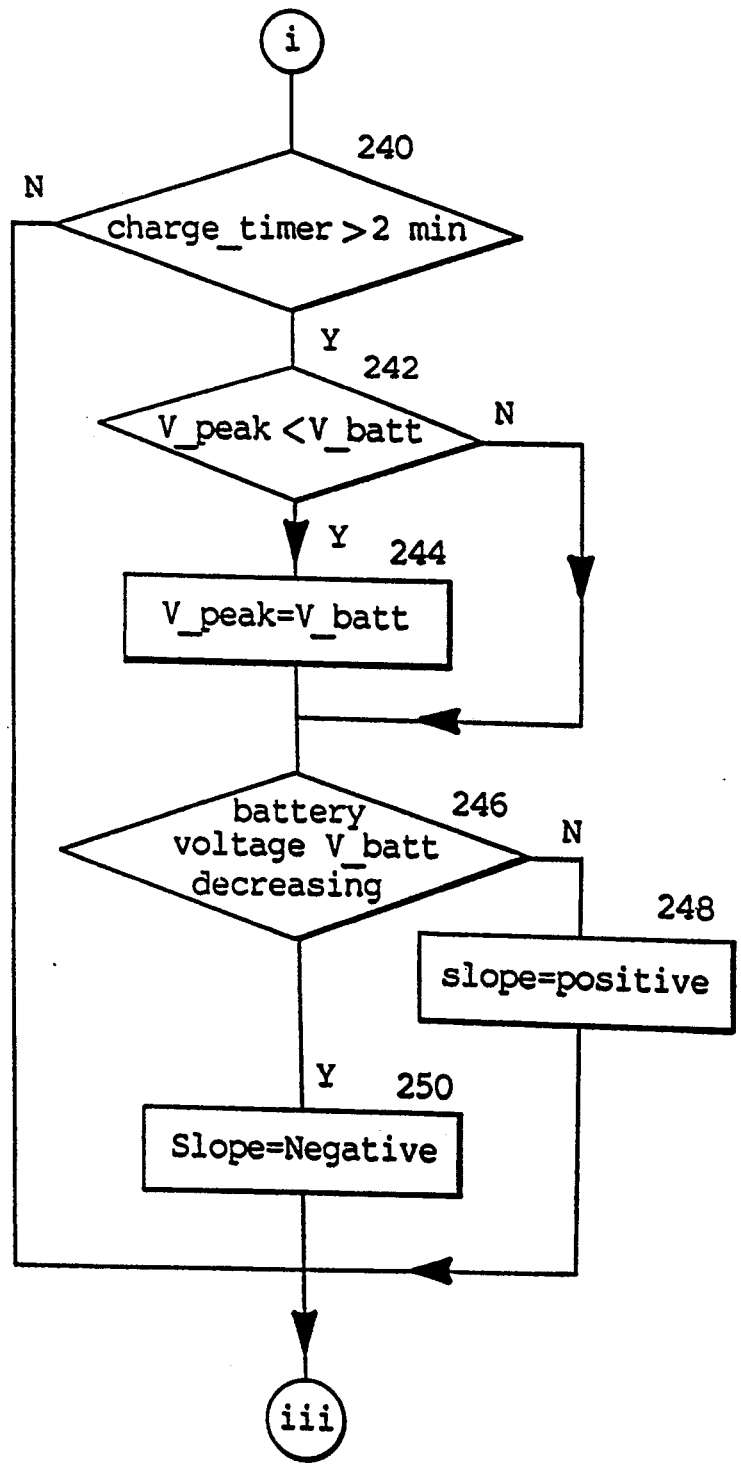

FIG 4Fiii CHARGE CONTROL
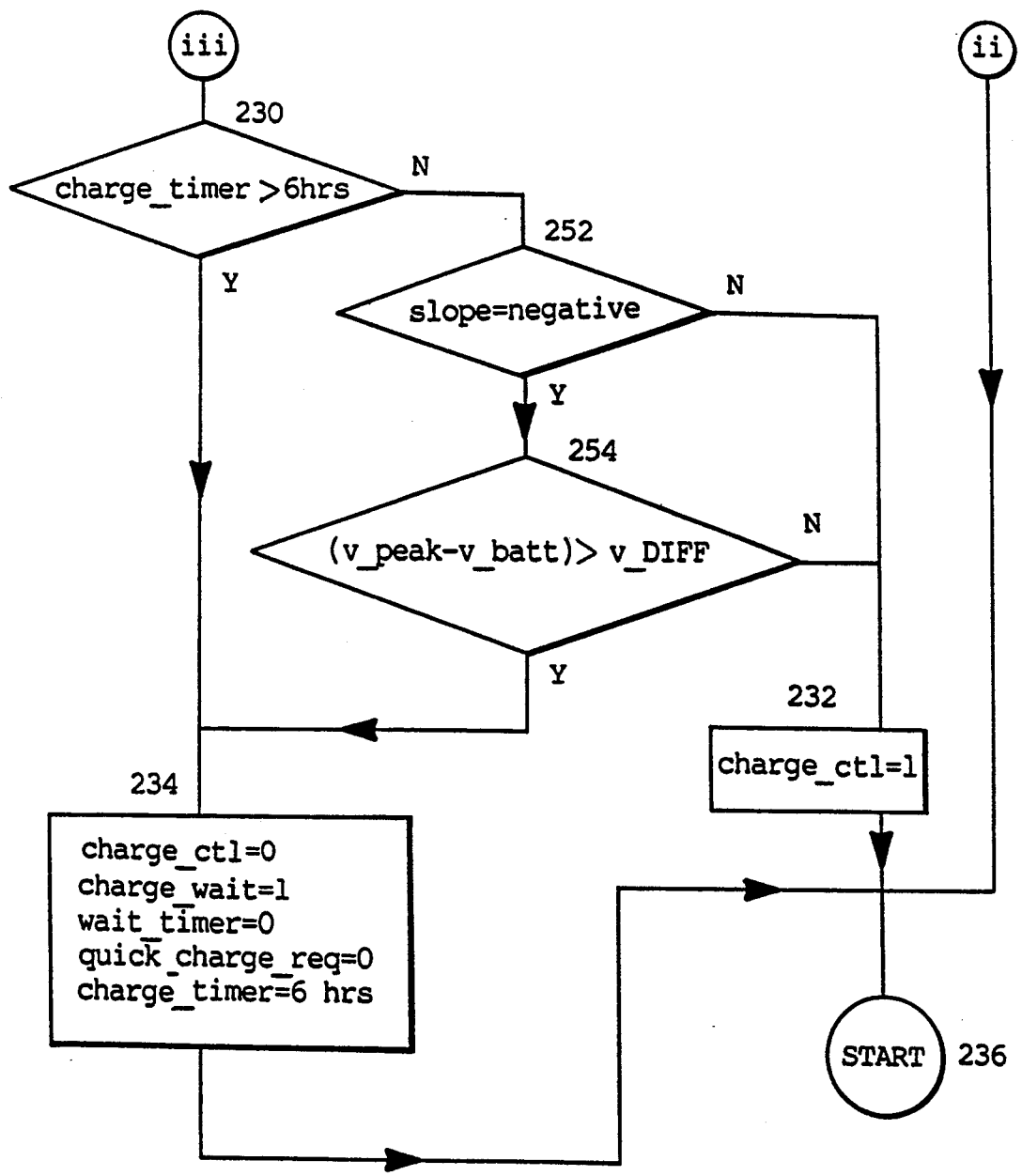

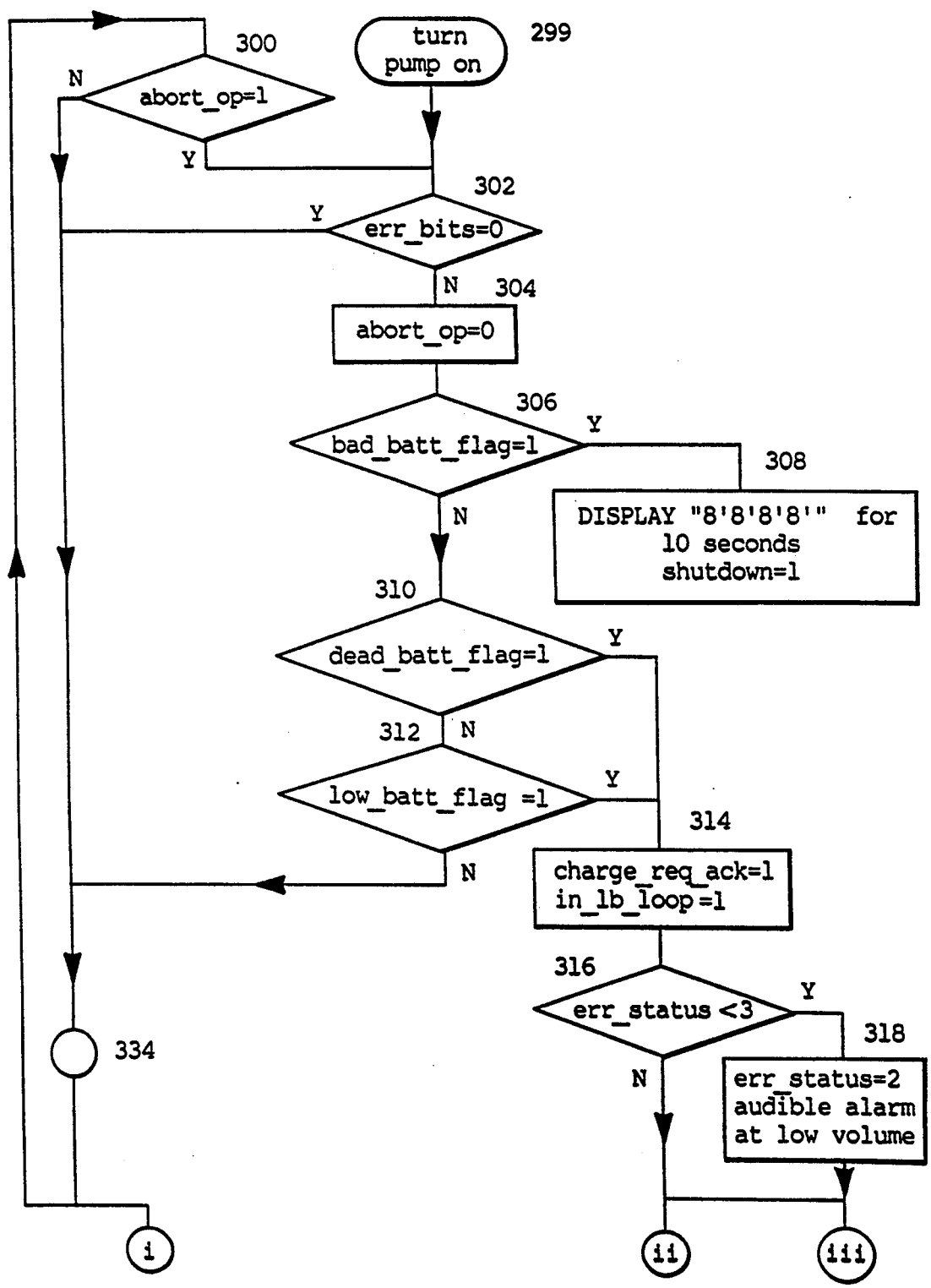

FIG 4Gii ERROR HANDLING
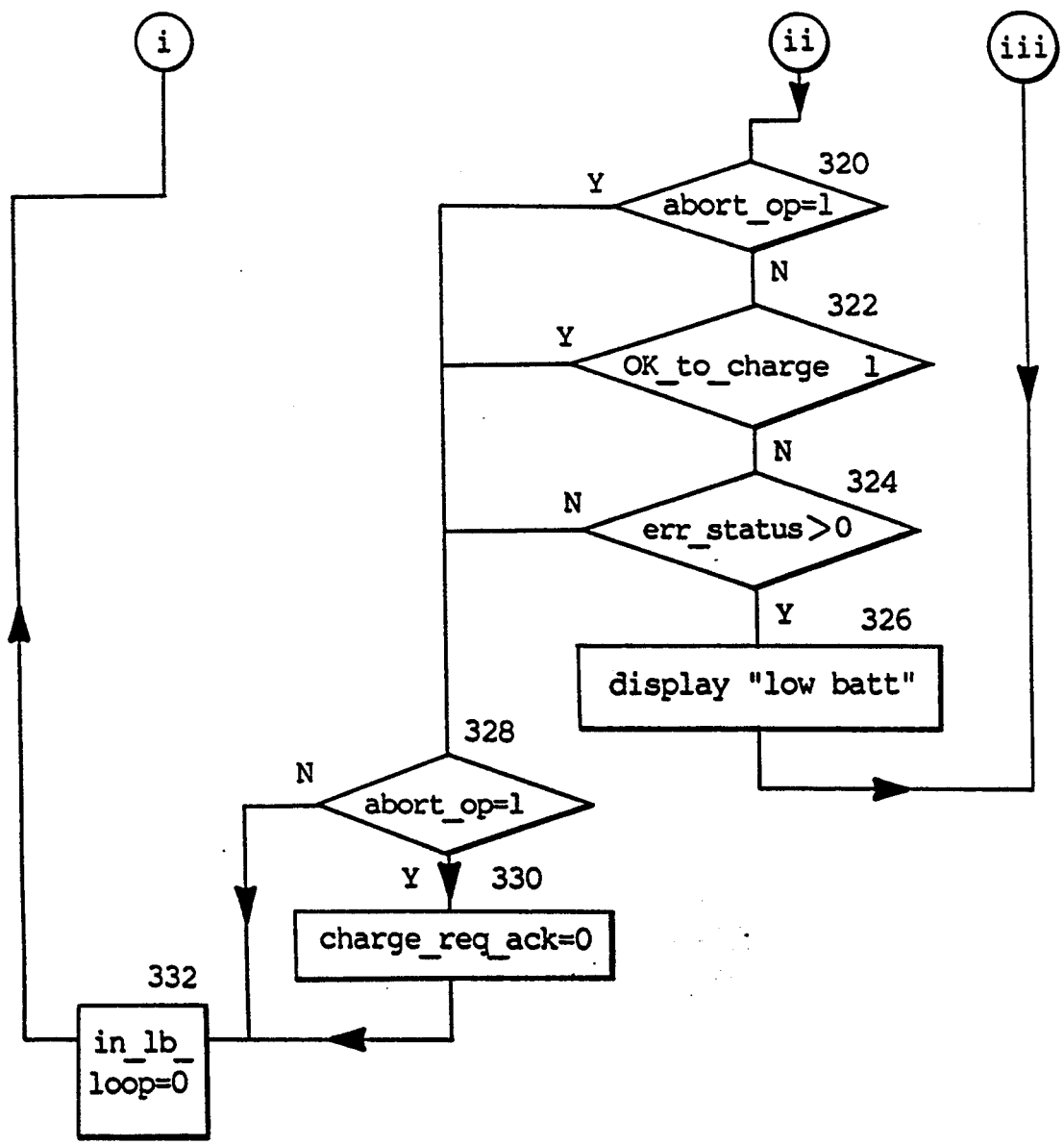

TYPICAL QUICK CHARGE V_BATT VS TIME-
QUICK CHARGE TERMINATED WHEN dV_BATT/dT <0
AND (V_PEAK_V_BATT) ≥ 60mV

BATTERY CHARGING CIRCUIT AND METHOD FOR AN AMBULATORY FEEDING PUMP

This application is a continuation-in-part of application Ser. No. 07/672,531 filed on Mar. 20, 1991 now abandoned.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to a circuit and method for charging batteries in a portable electrical or electromechanical device, such as an ambulatory medical device, where rapid charging is necessary, while protecting the integrity and reliability of the batteries. The invention specifically relates to a medical device, such as an ambulatory infusion pump, that requires reliable service from rechargeable batteries.

BACKGROUND OF THE INVENTION

Devices are known containing rechargeable batter having service times, i.e. the time between charging periods, of one hour to many hours. Most of these devices are equipped with a low battery alarm signal that may be audible or visual or both that indicates to the user that the batteries are nearly depleted and must be recharged promptly. The user may then attach the unit to a charger (which is connected to an AC outlet), or connect an internal charger to an AC outlet, for a recommended minimum time, after which the user may remove the unit from the AC outlet and expect the unit to be charged. Since the infusion pump may be administering life-sustaining fluids to the user, it is preferable to have the battery recharge time be as low as possible.

It is known in the art that rechargeable batteries may be recharged quickly by applying a "fast" charging current, i.e. a current approximating the maximum output current "C" of the battery. Unfortunately, along with the benefit of quicker charging comes the disadvantage of a potentially dangerous or battery-damaging condition or both. Battery life can be significantly shortened and excessive heat is often generated by overcharging the batteries. To avoid this situation, the known devices use a "trickle" charging current that is significantly less than C, perhaps C/10, such that the danger and possible damage are minimized, while tolerating the increased recharging time. "Quick" charging current levels are also known that are higher than a trickle charging current, but are still significantly less than C. The charging time is decreased with the quick charging current as compared to the trickle charge, and the danger and potential battery damage are reduced as compared to recharging the batteries at a current near C, but are not completely eliminated.

Thus, battery charging devices and methods exist that attempt to reduce the recharging time safely by using a plurality of charging currents during one recharging session. Such devices and methods are disclosed in U.S. Pat. Nos. 4,710,694; 4,394,611; and 4,240,022. One known method is to apply a quick charging current followed by a trickle charging current. The quick charging current can be applied until, for example, a time limit has run out, or a certain battery voltage has been reached, after which time the trickle charging current is applied.

One device is known that makes use of a quick charging current for recharging the batteries in an ambulatory medical device. This device, the FRESENIUS Frenta System has a feature described as "Rapid Charge." This feature allows the user to select a quicker charging current whenever desired. The higher charging current is then applied for a predetermined period of time, after which a trickle charge is applied.

Unfortunately, by giving the user control over the quick charging, several undesirable conditions can occur. For example, the user can select the quick charge and allow the batteries to be fully charged. The user removes the unit from its charging base, turns it on for ten minutes (a small fraction of the battery service time and power) and then reconnects the unit to its base and recharges the unit with another quick charge. The charging base will apply a quick charging current, rapidly bringing the batteries to their full charge level, while several hours of quick charge time remain. Although the danger is not excessive, the batteries will be damaged over time, greatly reducing their reliability, and eventually leading to battery failure.

It is thus an object of the invention to provide an improved battery charging device and method that decrease overall charging time, while protecting the batteries from damage.

It is a further object of the invention to provide a battery charging device and method that are automatic and immune to the inaccuracies of user control.

It is a further object of the invention to provide a battery charging device and method that increase the battery service time.

SUMMARY OF THE INVENTION

In accordance with the above-mentioned objects, the invention comprises a device having a rechargeable power source with an associated battery charger base having a quick charge current output and a trickle charge current output. A control circuit within the device is also provided that monitors if and for how long the device is attached to the base and determines the present capacity of the power source. Based on these signals, the control circuit selects an appropriate charge current output.

The foregoing and other objects and advantages of this invention will become apparent to those skilled in the art upon reading the detailed description of a preferred embodiment in conjunction with a review of the appended drawings.

BRIEF DESCRIPTION OF THE DRAWINGS

Preferred embodiments of the invention are shown in the accompanying drawings wherein;

FIGS. 4a, 4b, 4ci, 4cii, 4d, 4e, 4f, 4fii, 4fiii, 4gi and 4gii are a flow chart indicating the operating sequence of a charging method according to the invention;

DETAILED DESCRIPTION OF THE PREFERRED EMBODIMENTS

Figure 1:
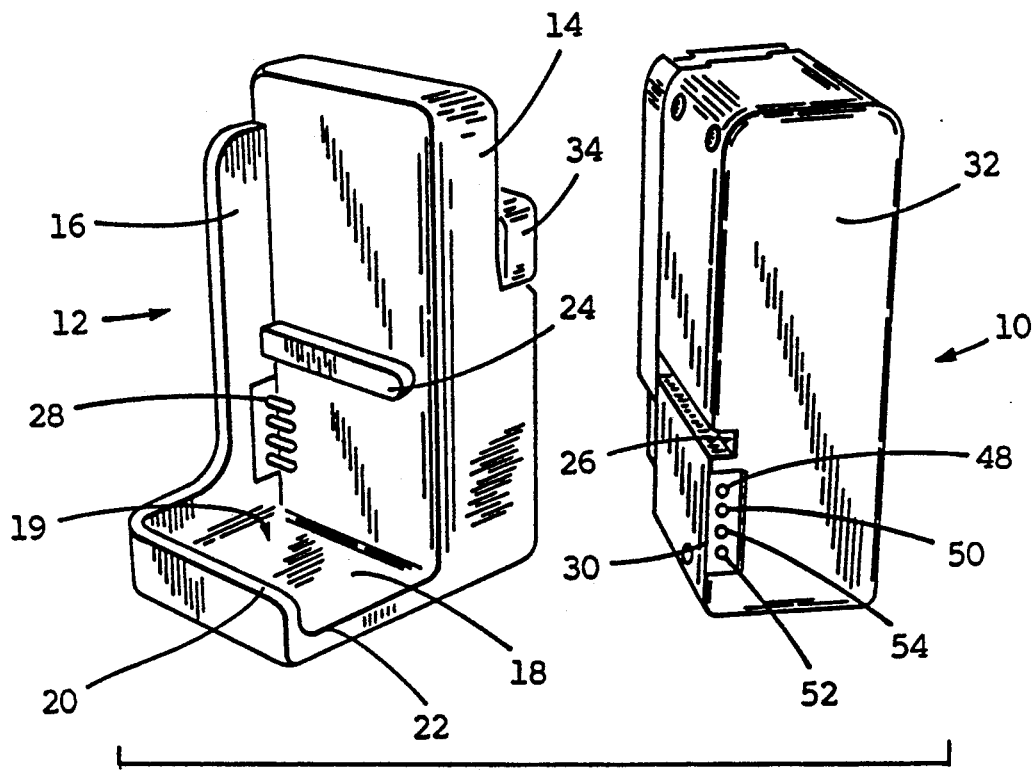
FIG. 1 is a perspective view of an infusion device and battery charger base according to the invention.

It is to be understood that while the invention is illustrated for a medical infusion pump, it can similarly be used in any electrical system having a rechargeable power source. Referring to FIG. 1, a medical infusion pump is generally designated by the reference numeral 10. A complementary charging base 12 is also provided. Within the base 12 is a circuit for supplying charging current to the pump 10, such as the circuit shown in FIG. 2.

Figure 2:
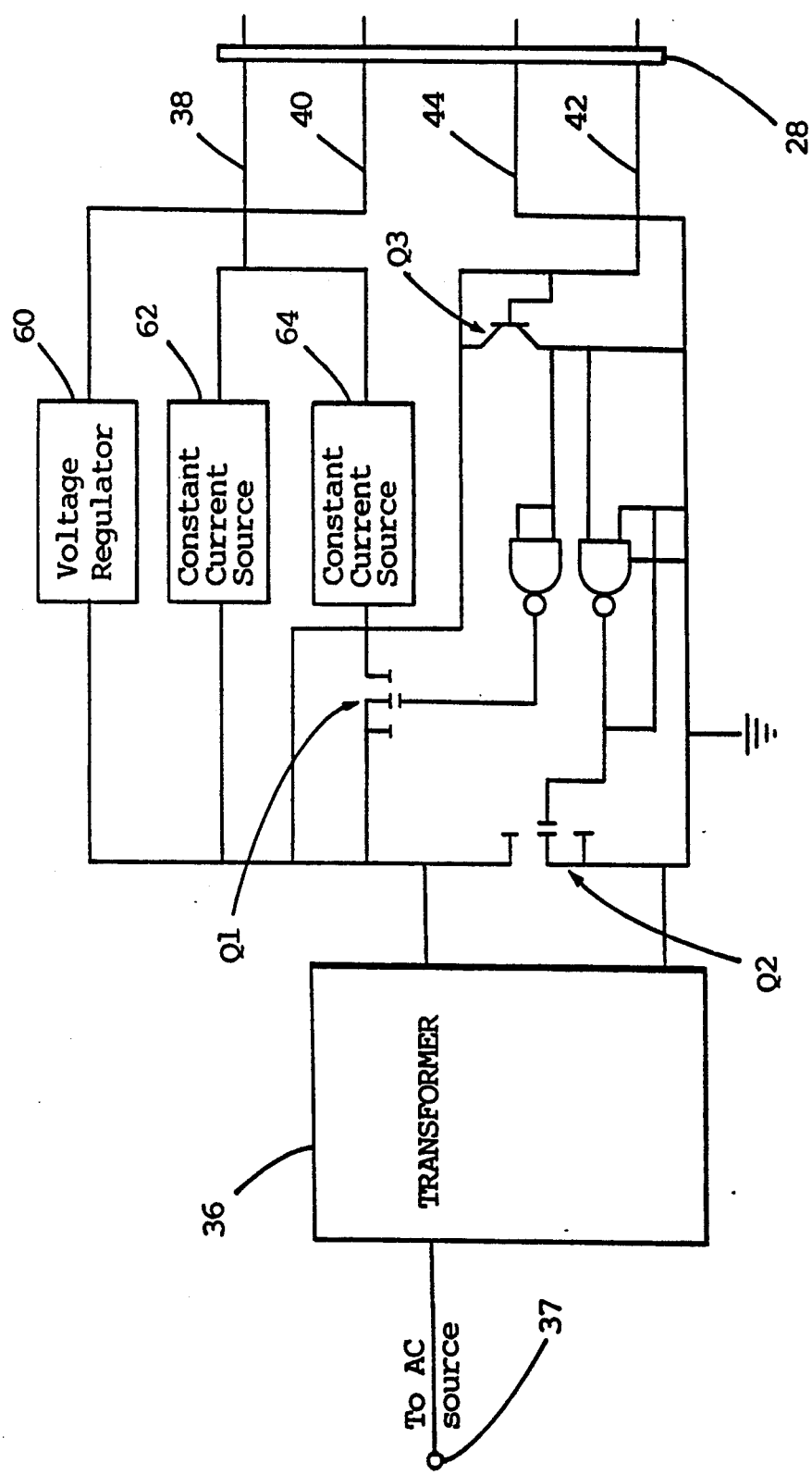
FIG. 2 is a schematic diagram of a portion of a battery charging circuit according to the invention.

The charging base 12 includes a housing 14 for containing the circuit in FIG. 2, and a side wall 16 and bottom floor 18 integral with the housing 14, forming a pocket 19 into which the infusion pump is mounted. The bottom floor 18 has a lip 20 that extends upward from the distal end of the bottom floor 18. The lip 20 is integral with the floor 18 and follows the distal edge of the floor 18 until it reaches and becomes integral with the side wall 16. The lip 20 does not extend to the side edge of the floor opposite the side wall 16, which thus forms an entrance 22 for the bottom infusion pump 10.

Figure 5:
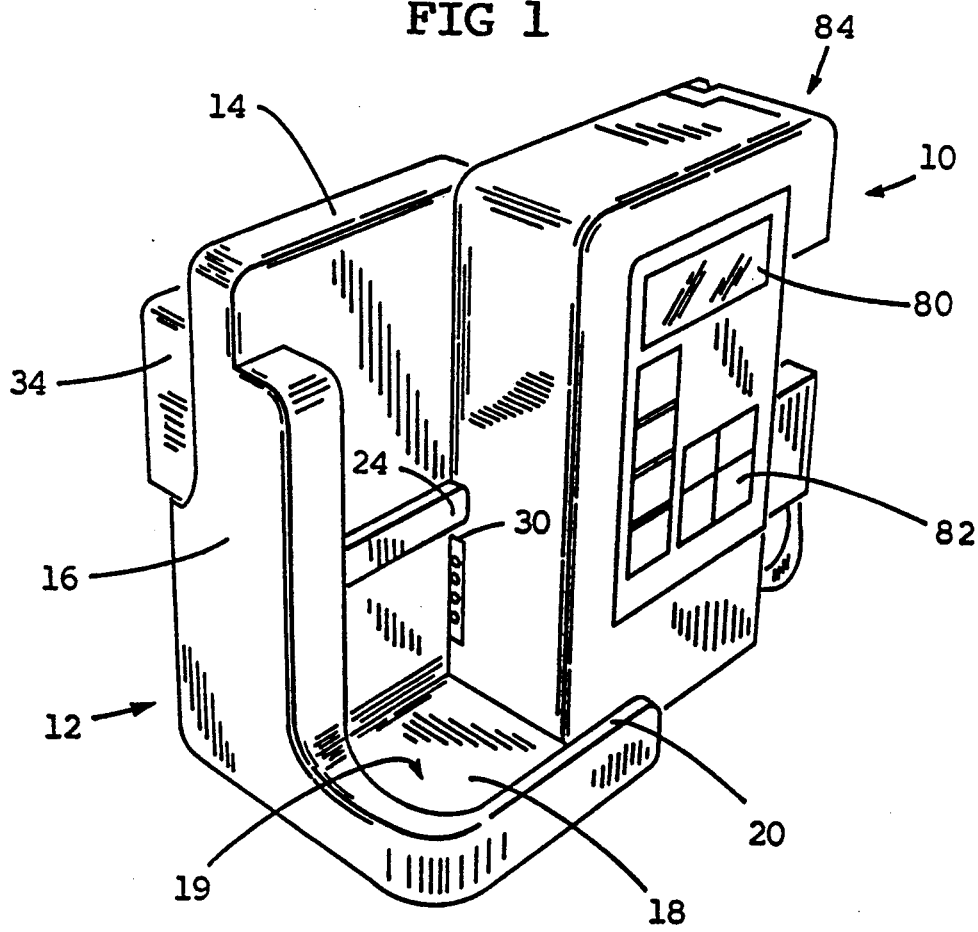
FIG. 5 is a perspective view of an infusion device partially mounted on a battery charger base.

Integral with the face of the housing 14 facing the pocket 19 is a guide bar 24 parallel to the bottom floor 18 and extending out of the housing 14. A corresponding guide groove 26 can be seen on the rear of the infusion pump which slidably receives the guide bar 24 when the infusion pump 10 is mounted on the base 12, as in FIG. 5. The size of the pocket 19 is dimensioned to closely fit the bottom of the infusion pump 10. When the infusion pump 10 is mounted to the base 12, the guide bar serves three functions: it aids in the proper alignment of the pump 10 with the base 12, prevents the pump 10 from being removed from any direction other than the entrance 22, and causes a slight compressive fit to frictionally retain the pump 10 against accidental detachment.

The male and female parts 28,30 of a four-pin connector assembly are mounted on the base 12 and pump 10, respectively. The male connector 28 is preferably mounted on the base 12 to decrease the likelihood of damage as compared to mounting on the ambulatory device. The male connector 28 is mounted on the interior of the side wall 16 of the pocket 19, as shown in FIG. 1. The female connector 30 is mounted slightly recessed on the side of the housing 32 of the infusion pump 10, in a position complementary to the male connector 28 when the pump 10 is fully engaged to the base 12.

The back of the housing 14 of the base 12 may include any attachment means, such as an IV pole clamp 34, for attachment to any desired surface. The housing 14 is also weighted sufficiently for use as a desk top base.

Figure 3:
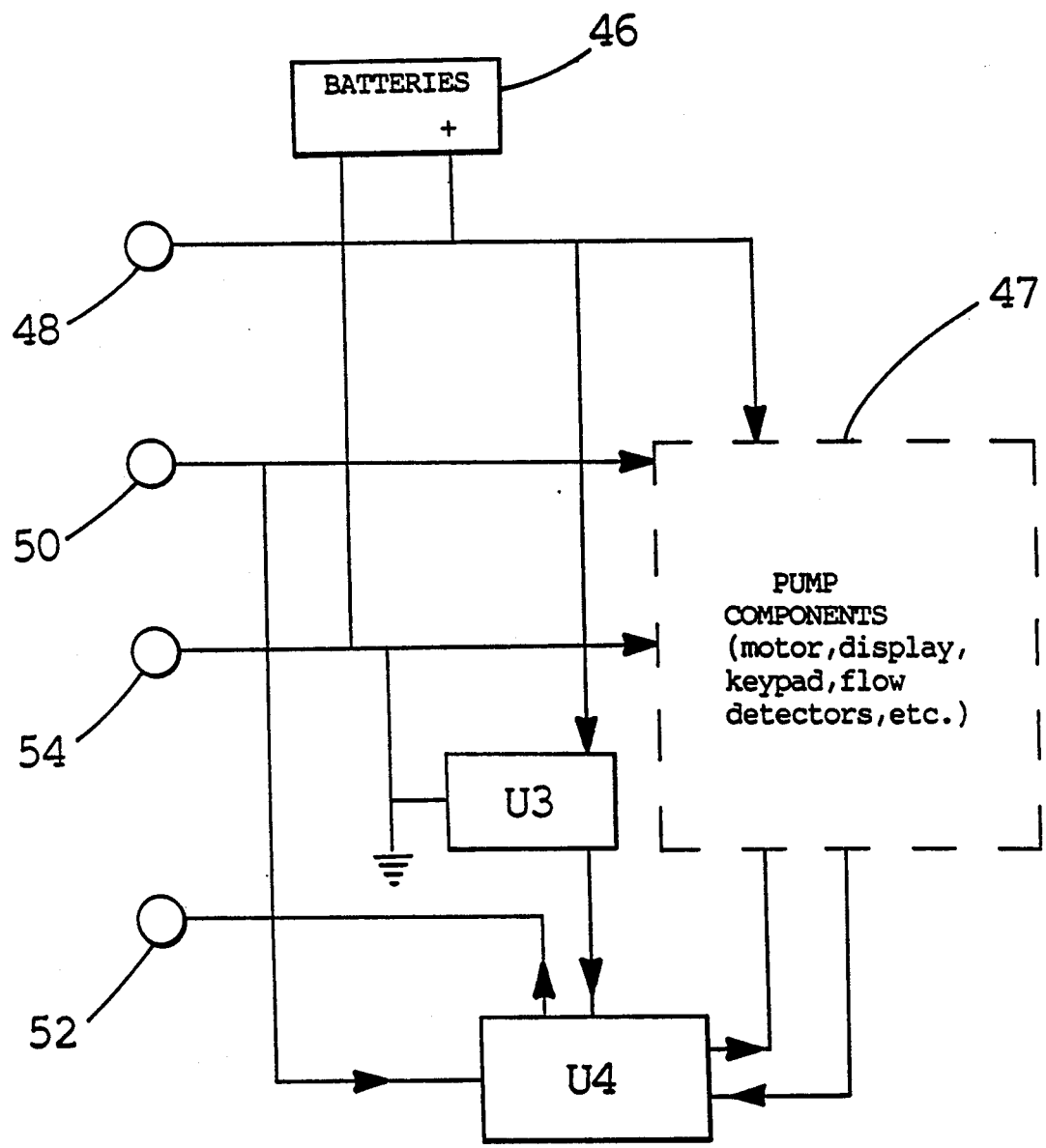
FIG. 3 is a schematic diagram of another portion of a battery charging circuit according to the invention.

The complete battery charging process through both circuits shown in FIGS. 2 and 3, is only active when the pump 10 and base 12 are attached. However, the control portion of the charging circuit, within the pump 10, performs several of the operations necessary for proper charging even with the base 12 detached, as will be explained further below.

The base 12 includes a charging current source circuit, such as that FIG. 2. The circuit is preferably connected through the housing 14 to an external conventional AC outlet (not shown), although other power sources will work similarly. Within the base, a transformer 36 is electrically connected to the AC outlet at 37. At the opposite end of the circuit in FIG. 2 are four connection lines 38, 40, 42, 44 for detachably connecting the circuit portion in the base to that in the infusion pump 10. These connections are a ground line 44, a regulated DC voltage line 40, a charging current line 38 and a charge control line 42. Each of these lines is electrically connected to one of the male pins 28 of the four-pin connector.

Between the transformer 36 and the four connection lines 38, 40, 42, 44 are circuit components designed to provide more than one charging current to the charging current line 38. In the preferred embodiment, there are two different charging currents, one for quick charging, the other for "trickle" charging. These two currents are preselected, based on known safe charging currents of the rechargeable batteries 46, which are housed inside the infusion pump 10. The quick charge current is preferably C/5, where C is the maximum output current of the batteries, while the trickle charge current is C/20. The trickle charge can be applied to the batteries for an indefinite period of time, without significantly damaging the batteries 46. The trickle charge maintains the batteries at their maximum charged condition despite the batteries inherent tendency to self-discharge when not being charged. The quick charge, however, can cause long-term damage to the batteries if applied for an excessive period of time. The regulated voltage at line 40 is supplied by voltage regulator 60.

The control portion of the charging circuit, shown in FIG. 3, which selects which of the two charging currents is applied to the charging current line 38, and the batteries 46 are housed within the infusion pump 10. The control circuit is integrated with other circuit components 47 for controlling the workings of the infusion pump 10, as some of the parameters for selecting the charging current are based on the functioning of 10. The main controller of the pump circuit is a forth four lead microprocessor U4, shown in FIG. 3, whose responsibilities include, among other things, controlling the motor (not shown), display 80, input terminals 82, and flow detectors 84, detecting connection of the base to the four-pin connector 30, and controlling the charging circuit in the base 12. call shown in FIG. 5).

In FIG. 1, the four female pin connections are shown: the charging current line 48; the regulated voltage line 50, which is used by the microprocessor U4 to detect the presence of the base 12; the ground line 54; and the charging current control line 52, which is a direct output from the microprocessor U4. The batteries 46, which are preferably three NiCad cells, are connected to both the charging current line 48 and the ground line 54 of the four pin connector. The batteries also power the circuitry and motor for the pump.

The control circuit monitors the present voltage level $V_B$ of the batteries 46, which gives an indication of their stored electrical energy capacity. The batteries are connected to an analog to digital (A/D) converter (U3 in FIG. 3), which converts the analog voltage into a stream of serial pulses in an 8-bit binary format and then transmits the stream to the microprocessor U4. The microprocessor uses this information to select an appropriate charging current, as is described below.

Figure 6:
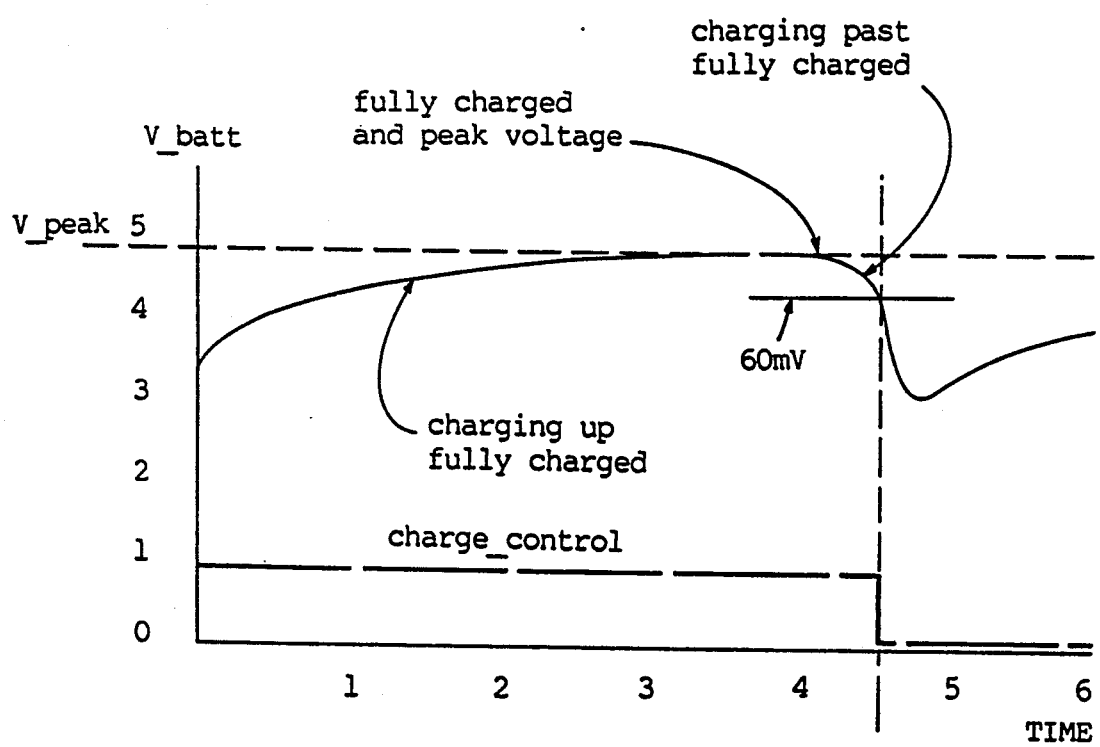
FIG. 6 is a graph of battery voltage versus time for one embodiment of the invention.

The microprocessor can also sense whether the pump is connected to the base. It simply detects the voltage at the regulated voltage line 50. Since the charging circuit in the base always maintains 5v at line 40, 5v is present at 50 if the base is connected. Of course, if the base is not attached to an AC outlet, there will be 0 v at 40, and the control circuit will consider the base to be absent whether it is connected or not. However, in the alternative, if the microprocessor U4 cannot use the regulating voltage line 50 for reasons including the lack of an available input/output port on the microprocessor U4, the presence of the base can also be detected through the analog to digital converter U3. Whenever the pump is attached to the base and electrical contact is made between the two, a detectable jump will occur in the battery voltage $V_B$, as at 70 in FIG. 6. Since no operation of the pump without the base would cause this jump, it can be used to sense connection to the base.

In operation, if the pump is connected to the base, the microprocessor U4 selects the appropriate charging current from the base by selectively applying 5 v to the charging current control line 52. When 5-v voltage is present at this line 42 of the charging circuit, the transistor Q3 is switched off. This causes the field effect transistor (FET) Q1 to turn off. Hence, only constant current source 62 is activated and a C/20 charging current is applied to the charging current line 38 and the batteries 46. When certain conditions are met, as described below, the microprocessor U4 applies ground voltage to the charging current control line 52, which switches on transistor Q3 of FIG. 2, which in turn switches on FET Q1 and constant current source 64, quadrupling the charging current to C/5.

For optimum safety and battery performance, it is preferable that when the battery capacity has dropped to below 30%, a quick charge is applied. At above 30% capacity, a full length quick charge (a maximum of 6 hours at C/5 in the preferred embodiment) can overcharge the batteries and cause long-term battery damage.

In the preferred embodiment, the batteries are at 30% capacity when their combined voltage equals 3.56 v. If the batteries are allowed to drain significantly after dropping below 30% capacity (for example, by continued pump use without recharging), they will reach the dead battery level of approximately 3.20 v, at which point the control circuit preferably shuts itself and the pump completely off.

To avoid long-term damage to the batteries, the control circuit within the pump ensures that after a complete quick charge, the base will not supply another C/5 quick charge for at least two hours, regardless of the battery capacity level, whether or not the unit is connected to the base, or the actions of the user. This two hour timer will be discussed in greater detail below.

Thus, by performing the operations described above, the following results and benefits are obtained. By having the ability to detect the presence of the charging base, the pump has greater flexibility and control over the charging current. This maximizes the quick charging times, but ensures safe charging of the batteries. After a full quick charge, the next quick charge cannot be initiated for two hours. If the six-hour quick charge is interrupted by removing the pump from the base, it can be restarted and also extended if power was drained during the unconnected interval.

It is also contemplated by the invention that multiple devices can be effectively charged with a single charger base. While one device is operated, a second device can remain on the base, charging according to the internal timers and circuit of the second device. When the first device is then attached to the base, it will be charged according to its internal timers, regardless of what charging current was applied to the second device. More than two devices may also be used. In this manner, each device is charged most effectively for maximum service time of each device. Referring to FIGS. 4a–4g, the following operating steps, much of which occur within the microprocessor, will describe the preferable mode of the operation. The steps of the flow chart have been given reference numerals for identification purposes.

Appendix I lists the bits and registers used in the software described in FIGS. 4a–4gii. The use of these bits and registers is also described in Appendix I to aid in an understanding of the operation of the software.

Two "loops" of software, steps 110–236 and steps 300–332, are run at the same time. While the program is running through steps 110 to 236, the program is simultaneously running through a loop comprising steps 300 to 332 which handles any error indicators that may be generated by the operation of the program and displays the appropriate error messages.

At step 110 in FIG. 4A, the control routine is initiated within the microprocessor U4 every 500 milliseconds. During the 500 millisecond interval, the program passes from step 110 to step 236 which restarts the program at step 110 after the 500 millisecond interval is completed.

From step 110, the program passes to step 112. The first operation at step 112 is to write the value of register v_batt to register v_last. Then, the battery voltage $V_B$ is read through the A/D converter U3 and written to register v_batt. Since the value of register v_batt is placed in register v_last before it is updated to the currently measured value of $V_B$, upon exiting step 112, register v_last will contain the value of the battery voltage measured on the immediately previous pass through the software while register v13 batt will contain the current measured battery voltage $V_B$. From step 112, the program passes to step 114.

At step 114, it is determined whether the bit bad_batt_flag has been set, thereby indicating whether a bad battery has already been detected on a previous pass through the software. Throughout this description, a reference to a bit being "set" means that the bit contains the value "1". Likewise, "latched" as used in this description means that the register is set to contain the value "1" or other specified non-zero number depending on the type of register. Of course, a bit or register may be "set" or "latched" as well as "un-set" or "un-latched" as needed as the program operates.

If, at step 114, bit_bad_batt_flag has been set, indicating that the program has previously determined on a previous pass through the software that the battery voltage $V_B$ is outside the acceptable limits, the program passes directly to step 122 and avoids redetermining whether the battery voltage $V_B$ is outside the acceptable limits. If bit bad_batt13 flag has not been set, the program passes to steps 116, 118 and 120 to determine whether to set bit bad13batt13flag. At step 116, if the battery voltage $V_B$ is greater than 4.9 v, indicating that the battery voltage is excessive, the program passes to step 120 where the bad_batt_batt flag bit is set.

If at step 116, the battery voltage $V_B$ is not greater than 4.9 v, the program passes to step 118 where the battery voltage $V_B$ is compared to the low threshold value of 2.6 v. If $V_B$ is less than 2.6 v, this indicates a bad battery is present so the program passes to step 120 where the bad_batt_flag bit is set.

If, at step 118, $V_B$ is not less than 2.6 v, this indicates that the battery voltage $V_B$ is greater than or equal to 2.6 v and less than or equal to 4.9 v, which means that the battery voltage $V_B$ is in an acceptable operating range. Consequently, there is no need to set the bad_batt_flag bit. Therefore, if, at step 118, the battery voltage $V_B$ is not less than 2.6 v, the program passes to step 122.

At step 120, in addition to latching the bad_batt_flag bit, the quick_charge_req and low batt flag registers are both latched to later trigger the appropriate response to the bad battery condition. Also at step 120, the value 14 minutes and 50 seconds is placed in register batt15_timer. Execution of step 120 occurs only once after detection of battery voltage $V_B$ outside the range of 2.6–4.9 v described above. Thereafter, the bad_batt_flag bit is set the program will bypass steps 116 through 120 passing from step 114 directly to step 122. From step 120, the program passes to step 122.

Steps 122 through 128 determine whether a dead battery condition exists. By dead battery condition, it is meant that the battery voltage is less than 3.20 v. At step 122, bit dead_batt_flag is evaluated to determine whether it has already been determined on a previous pass through the software that a dead battery exists. If it has already been determined that a dead battery exists, bit dead_batt_flag will already be set so that the program passes from step 122 directly to step 130 in FIG. 4B. If bit dead_batt_flag has not already been set, the program passes from step 122 to step 124 to begin a loop which determines whether to set bit dead_batt_flag.

At step 124, bit ok_to_charge is evaluated to see whether it is set, thereby indicating that the pump is connected to the operating charge base. If bit ok_to_charge has been set, the program passes from step 124 directly to step 130 so that charging of the batteries may take place. If ok_to_charge has not been set, the program passes to step 126 where the battery voltage, $V_B$, is compared to the dead battery threshold of 3.20 v. If at step 126, the battery voltage, $V_B$, is greater than or equal to 3.20 v, the program passes to step 130. If the battery voltage, $V_B$, is below the threshold of 3.20 v the program passes to step 128 where the dead—batt_flag bit is set. Execution of step 128 occurs only once after detection of a battery voltage $V_B$ below the dead battery level of 3.20 volts. Also at step 128, the quick_charge_req and low_batt_flag bits are set and the register batt15_timer has the value 14 minutes and 50 seconds placed in it.

Steps 120 and 128 contain common code that enables subsequent software to determine whether an error condition exist and to display an appropriate error message indicating the status of the batteries. The low_batt_flag and quick_charge_req bits are set to enable generation of error messages and batt15_timer is latched to contain a preset time of 14 minutes and 50 seconds.

The register batt15_timer performs three functions. First, it times a 15 minute pumping time after the detection of a low battery or bad battery condition before the microprocessor shuts off the pump. This allows the user of the pump sufficient time to disconnect the pump from whatever use it is being put to and get it to a charger. Shutting off the pump ensures that the batteries will not be discharged to the point where they will be permanently damaged.

The second use of the batt15_timer is to time when the final error messages are displayed prior to shutting off the pump. When steps 120 or 128 put the value 14 minutes and 50 seconds placed in batt15_timer due to a bad or dead battery error detection, the program will direct a 10 second bad battery error message to be displayed before the microprocessor shuts itself and the pump down as the value in batt15_timer reaches 15 minutes. Used in this way, register batt15_timer shortcuts the operation of steps 152 and 154 as will be explained hereafter.

Finally, if the value of batt15_timer is less than 14 minutes and 40 seconds and the low battery condition has been detected so that the low_batt_flag bit is set, the program will give a low battery warning message until acknowledged by the pump user. When the batt15_timer has the value of 14 minutes and 40 seconds, a final 20 second warning message is given before the pump is shut off.

Steps 120 and 128 differ in that step 120 sets the bad_batt_flag bit, indicating the presence of a bad battery, while step 128 sets the dead_batt_flag bit indicating the presence of a dead battery. From step 128, the program passes to step 130.

In steps 130 through 139 in FIG. 4B, the microprocessor checks for previous acknowledgement of a low battery condition and for previous use of the charging base. At step 130, the battery voltage, $V_B$, is compared to a low battery threshold, 3.35 v. If the battery voltage $V_B$ is greater than or equal to 3.35 volts, indicating that the battery voltage $V_B$ is not low, the program passes from step 130 to step 140. If at step 130 $V_B$ is less than 3.35 v, indicating that the battery voltage $V_B$ is low and that a quick charge may be desirable, the program passes to step 132.

At step 132, it is determined whether the pump is attached to the charge base. If bit ok_to_charge is set indicating the pump is connected to the charge base, the program passes to step 139 where the low_batt_flag bit is set so that charging of the batteries may be initiated. From step 139, the program passes to step 140 in FIG. 4C. If, at step 132, the pump is not in the charge base so that the ok_to_charge bit is not set, there is no need to try to charge the battery so the program passes to step 134.

At step 134 it is determined whether the pump is turned on as indicated by the turn_on bit being set. To the user, the pump being turned on means that the pump's display is on. Whether the display is on or not, the microprocessor continues to run the timers and pass through the program. If the pump is turned on, the turned_on bit will be set and the program passes to step 136. If, at step 134 the pump is not turned on, as indicated by the turned_bit not being set, there is no way to indicate an error condition, so the program passes to step 139.

At step 136 it is determined whether a quick charge request has previous been acknowledged. If a quick charge request has been previously acknowledged, the charge13 req13 ack bit will be set. If the charge_req_ack bit has been set this indicates that the microprocessor is requesting a quick charge to the batteries. In this case, the program passes to step 139. If the charge_req_ack bit is not set, the program passes to step 137.

At step 137, it is determined whether a previous low battery condition has been detected. If it has, bit low_batt_flag will be set. In this case, the program passes to step 139 and will not execute step 138 which would cause another display of the LOW BATT error message. If bit low_batt_flag is not set, the program passes to step 138.

It should be noted that in order to get to step 138, the pump must not be in the charge base, it must be turned on, it must not have had a quick charge request previously acknowledged and it must not have already detected the low battery condition. At step 138, bit abort_op is set to indicate that the error condition "the pump is not connected to the charger" exists. From step 138, the program passes to step 139.

As can be seen, despite the variety of ways of getting to step 139 as described above, step 139 sets bit low_batt_flag as a result of the detection at step 130 that the batteries have a low battery voltage $V_B$.

Steps 140 through 174 in FIGS. 46ii, 46ii and 4B generate the triggers for the various error conditions. At step 140, the microprocessor checks the low_battery_flag bit to see if it is set, thereby indicating that the batteries are low. If this flag has not been set by previous tests of the battery voltage $V_B$, the program passes directly to step 176. Otherwise, the program has determined that the batteries are low and the program passes to step 142 to determine if error conditions exist. At step 142, if a quick charge has not previously been requested so that the quick_charge_req bit is not set, the program passes to step 144 where step 144 is executed. However, if the quick_charge_req bit has already been set, the program by-passes step 144 and passes directly to step 146.

Step 144 resets register batt15_timer to zero minutes, which allows the pump to run for 15 minutes after the detection of a low battery state before the microprocessor turns the pump off. In addition, register charge_timer, which is used to time the 6 hour quick charge cycle, and the charge_req_bit are reset to zero. Register charge_timer can be thought of as a gas tank for charge to power the pump. By resetting this register, the full amount of charge time may be requested because the charge "gas tank" is empty. Further, register quick_charge_req is set to latch these newly set parameters and to indicate to subsequent software that a quick charge is needed. The program then passes to step 146.

At step 146, microprocessor U4 tests for the presence of the charge base by looking at the value of bit ok_to_charge. If this bit is set, indicating the presence of the charge base, the program passes to step 148. At step 148, the program determines whether the batteries are bad by looking at the value of the bad_batt_flag bit. If the bit is set, indicating the batteries are bad, the program passes to step 152. Otherwise, the program passes to step 160. Note that in order to get to step 160 the batteries must be low, but not bad and the charge base must be connected to the pump. If the charge base is not connected to the pump so that the ok_to_charge bit is not set, as indicated at step 146, because the batteries are low, as indicated at step 140, it may be desirable to have a quick charge, but an error condition exists. In this case, the error condition is that the pump is not connected to the charge base. Therefore, at step 146, if the ok_to_charge bit is not set, that is, the pump is not connected to the charger base, the program passes to step 152. If the pump is connected to the charger base but the batteries are bad, an error condition exists so the program also passes to step 152 from step 148.

If the pump is connected to the charge base and the batteries are not bad, the program passes from step 148 to step 160. At step 160, the microprocessor resets bits low_batt_flag, dead_batt_flag, and charge_req_ack and register batt15_timer to zero. This action ensures that a bad battery or dead battery error message will not be accidentally generated since the pump is connected to the charger base. This also allows the microprocessor to issue subsequent low battery errors when the pump is removed from the charger base. Battery charging at the C/5 rate will then be enabled and will eventually be executed at step 232. From step 160, the program passes to step 176.

Step 152 increments the value in the register batt15_timer so that batt15_timer acts like a clock. Note that in order to get to step 152, a low battery condition must have first been detected at step 140. One possible set of conditions that would get to step 152 is to have a low battery as detected by step 140 and to have the pump not connected to the charger as detected by step 146. In this case, as mentioned above, the program allows 15 minutes for the pump to operate before it must be connected to the charger unit in order to avoid damage to the batteries before the microprocessor shuts down the pump.

The other way to get to step 152 is for the batteries to be low as detected at step 140 and the pump is connected to the charger as determined by step 146, but the batteries are bad as determined by step 148 in this way of entering step 152, incrementing step 152 also allows the pump to be used for up to 15 minutes after the detection of the bad battery condition. However, subsequent programming causes an error message to be displayed indicating the presence of a bad battery. From step 152 the program passes to step 154.

At step 154, the value of register batt15_timer is evaluated. If the value in the batt15_timer is less than or equal to 14 minutes and 40 seconds, the program is still well within the 15 minute grace period given for operation of the pump after the detection of a low or dead battery condition before the microprocessor shuts oft the pump. If the value of the batt15_timer is greater than 14 minutes and 40 seconds, the 15 minute grace period is about to expire. Therefore, the pump is in the process of displaying the final 20 second or less error message indicating that the pump is about to be turned off because the 15 minute grace period is about to expire. Therefore, at step 154, if the value in the batt15_timer is less than or equal to 14 minutes and 40 seconds, the program passes from step 154 to step 172 to allow charging to take place if necessary. However, if the value in the batt15_timer is greater than 14 minutes and 40 seconds, the program passes to step 155.

Step 155 examines the value in the err_status register. The err_status register is a countdown counter which controls when the audible beeper comes on. Detection of an error of any kind causes the err_status to be set to 2. If the value is less than three, that is 2, the program passes to step 158 where register err_status is set to a value of 255. Setting the err$_{13}$ status register to 255 causes an audible alarm to sound at full volume. Further, setting register err_status to 255 ensures that on subsequent passes through the software, at step 155 the value in register err_status will be greater than 3. In this case, the program will by-pass step 158, since the error message generated by step 158 is already being generated, and pass to step 156. In addition, step 158 cancels all non-battery error flags to prevent interruption of imminent shut down of the pump. From step 158 the program passes to step 162.

If, at step 155, the err$_{13}$ status register has a value greater than 2, which will occur as a result of already having passed through step 158 in a previous pass through the software, the program passes to step 156 where the bad_batt$_{13}$ flag bit is tested. The only way to get to step 156 is by being in the last 20 seconds of the 15 minute grace period after the detection of a low battery condition or in the last 10 seconds of a dead battery or bad battery error condition. The purpose of step 156 is to differentiate between the low battery and the bad battery error conditions and the dead battery error condition. In the preferred embodiment of the software, the error message for the low battery and the dead battery condition is the same as will be explained hereafter. However, the error message for the bad battery is different. If the bad_batt_flag bit is not set, indicating that the batteries are either low or dead, the program passes directly to step 170. If the bad_batt— flag bit is set, indicating the error condition of bad batteries, the program passes to step 157 where the in_bad_batt bit is tested.

The purpose of the in_bad—batt bit is to determine whether the loop of the program which displays the bad battery message has already been started. Once this loop has been started, the in_bad_batt bit will be set. If this register is not set, indicating that bad battery message is not being displayed because this is the first pass through the software after detecting the bad battery condition, the program passes to step 158 where the err_status register is set to 255, an audible alarm is sounded at full volume and all non-battery error flags are cancelled. If the in_bad_batt bit is set, indicating that the bad battery message is already being displayed, there is no need to initiate the error message so the program passes from step 157 to step 170.

The tests of steps 156 and 157 allow the generation of the higher priority BAD BATT message even if LOW BATT is already being displayed. The tests of steps 155, 156, and 157 also latch the variable in register err$_{13}$.status$_{13}$ set in step 158 to a value much greater than 3, thereby allowing this variable to be set only one time on the first pass through the program after the detection of this error condition. This in turn only enables battery-related error messages to be displayed by the error handler part of the program.

To get to step 162, the program must have just passed through step 158. Because of the action of step 155 described above, the program will pass through step 158 on the first pass through the program after the first detection of an error message. Step 158 will initiate an error message indicating that the batteries are low, bad or dead.

Because the program continuously loops, as described above, after the low or dead battery message or bad battery message has been started, the program will continue to loop every half second while displaying the 20 second low battery message or the 10 second bad battery or dead battery message. Consequently, the program passes to step 158 only as the 20 second low battery message or the 10 second bad battery or dead battery message is initially started. Thereafter, because the register err$_{13}$status is given the value of 255 in step 158, as the program subsequently loops, at step 155, the program will pass from step 155 to step 156 and thereby avoid step 158.

Step 162, tests whether or not the microprocessor is already in the loop of the program that displays the LOW BATT message. Step 162 does this by looking at the contents of the in_low_bat_loop bit. If this bit is not set, this indicates that the microprocessor is not in the loop that displays the LOW BATT message. This means that the program is about to display the low battery error message. Therefore, the program passes to step 168. If the flag is set, the program is already displaying the low battery error message and the program passes to step 164.

Step 164 tests whether the microprocessor is displaying the higher priority BAD BATT message. This is done by looking at the value of the in_bit_batt loop bit. If the bit is set, the BAD BATT message is displayed through the action of step 308, as will be described hereafter, and the program passes to step 170. If the register is not set, the BAD BATT message is not displayed and the program passes to step 166.

Step 166 determines if the bad_batt_flag bit has been set in response to a determination that the batteries are bad. If the bad_batt_flag bit is set, the program passes to step 170. If the bad_batt_flag bit is not set, the program passes to step 168 where the abort_op bit is set. The abort_op bit being set is a signal to the rest of the program to orderly shut down the current operation and proceed to the error handler shown in the flow chart of FIG. 4g. From step 168, the program passes to step 170.

Step 170 resets bit charge_req_ack to zero and sets the err_status counter to 255. Setting the register err_status to 255 disables acknowledgement of LOW BATT, DEAD BATT, and BAD BATT with the keypad. Resetting the charge_req_ack allows the program to acknowledge a low or dead battery condition when the pump is connected to the charger base. The program then passes to step 172.

At step 172, the value of batt15_timer is evaluated. When the value in batt15_timer exceeds 15 minutes, the program passes to step 174 where the bit shutdown is set, causing the microprocessor to stop all program execution to save the batteries from damage by being overdrained. If the value in register batt15_timer is less than or equal to 15 minutes, the program passes directly from step 172 to step 176.

FIG. 4e shows a flow chart for compensation of the register charge_timer to account for pump usage and comprises steps 176 through 198. The microprocessor determines how much power is being drained from the battery by accessing the conditions of operation of the pump as will be described hereafter. Depending on the amount of charge being drained from the batteries, the microprocessor will subtract an appropriate amount of time from the register charge_timer to increase the duration of the subsequent C/5 charging, up to a maximum of 6 hours. This part of the program begins at step 176 by the microprocessor checking for the presence of the charger base by looking at the value of bit ok_to_charge. If the charger base is connected, the ok_to_charge bit will be set and the program passes to step 178 to begin the part of the program which directs which type of charging to do.

At step 178, register charge_timer is tested to see if it has a value less than 6 hours. Having a value greater than or equal to 6 hours is called a "timeout". If this "timeout" has occurred, this indicates that the batteries have already been quick charged for their full 6 hours. Consequently, only trickle charging is allowed and the program passes to step 200 (shown in FIG. 4f) where the default setting of zero of bit charge_ctl allows the trickle charging to occur.

If the "timeout" has not occurred, register charge_timer will have a value less than 6 hours. Consequently, the program passes from step 178 to step 180. At step 180, because there is some amount of time remaining that the batteries will quick charge when enabled, the charge$_{13}$ wait register is tested to see if it is set. If it is set, 2 hours have not elapsed since the previous quick charge. Consequently, only trickle charging will be allowed so the program passes from step 180 to step 184. At step 184, the register charge$_{13}$ timer is incremented every other pass through the program, that is, every second, to account for the time passed since the last quick charge. From step 184, the program passes to step 200.

If bit charge_wait is not set at step 180, it has been more than 2 hours since the last quick charge so it is permissible to quick charge the battery. Consequently, the program passes from step 180 to step 182 where the bit quick_charge_req is tested. If bit quick_charge_req bit is set, indicating that a quick charge request has been made, because the program at this step qualifies for quick charging, the program passes to step 186 for quick charging. While at step 186, the register charge_timer is incremented every pass through the program, that is, every ½ second to keep track of the quick charge time. If at step 182, a quick charge request has not been made, the program passes to step 184 for trickle charge timing as described above. From both steps 184 and 186, the program passes to step 200.

If, at step 176, the pump is not connected to the charge base so that bit ok_to_charge is not set, the program passes to step 188 where register charge_timer is tested. If this timer is equal to zero, this indicates that the batteries are depleted so it cannot be decremented further. As a result, the program passes from step 188 directly to step 200.

If register charge_timer contains a value greater than zero, this indicates that some charge remains in the batteries. As a result, the program passes from step 188 to steps 190 through 198 where register charge_timer is decremented in a manner proportional to the pump activity. Step 190 tests bit turned_on to determine if the pump is turned on. If the pump is off, the timers will still be running but no display is activated or motor running. In this case, bit turned_on will not be set thereby causing the program to pass to step 194. Step 194 recognizes that because the pump is turned off, the drain on the batteries will be reduced. As a result, step 194 decrements register charge_timer only once every 11 seconds, so that this low-level drain on the batteries charge will be appropriately compensated for in register charge_timer. From step 194, the program passes to step 200 in FIG. 4F$i$;

If the pump is turned on at step 190, bit turned_on will be set and the program passes to step 192. At step 192, the microprocessor tests bit motor_ctl to determine if the motor is rotating at that time. When the motor is rotating, bit motor_ctl will be set. If the motor is not rotating, the drain on the batteries will be less then if it were rotating. Consequently, if bit motor_ctl is not set. the program passes to step 198 where register charge_timer is decremented every 2 seconds to appropriately compensate for the charge drain from the batteries. From step 198, the program passes to step 200.

If the motor is rotating so that bit motor_ctl is set, the pump is drawing charge from the batteries for the operation of the microprocessor, the display and the motor. This condition produces the biggest drain on the batteries of all the conditions of steps 190 through 198. As a result, the program passes from step 192 to step 196 where register charge_timer is decremented every 1 second. From step 196, the program passes to step 200.

Step 200 in FIG. 4F$i$; begins the software that actually controls the charge output of the charger base through a microprocessor I/0 line. Step 200 tests the bit charge_wait to determine whether the required 2 hour time interval has elapsed between quick charges. If the required time has elapsed, quick charging is possible and register charge_wait has not be set so the program passes to step 222.

At step 222, bit quick_charge_req is checked to see if a quick charge has been requested as indicated by bit quick_charge_req being set. If not quick charge has been requested, bit quick_charge_req will not be set so the program passes from step 222 to step 228 where bit charge_ctl is cleared. This bit is cleared because in order to get to step 228, quick charge must not have been requested. Therefore, clearing bit charge_ctl ensures that quick charge will not be sent to the batteries. Thereafter, the program passes to stop 236 to implement the timing sequence that causes the program to pause before reentering the program at step 100 so that the program operation begins every ½ second.

If, at step 222, a quick charge has been requested so that bit quick_charge_req is set, the program passes to step 224 where bit ok_to_charge is tested for the presence of the charger base so that quick charging can begin. If the base is not connected to the pump, bit ok_to_charge will not be set so the program passes to step 226 where bit charge_ctl is cleared, and bit slope_2 is cleared which indicates that the battery voltage $V_B$ is increasing.

Resetting bit charge_ctl at step 226 acts as a safety valve because a quick charge request has been requested but the pump is not connected to the charger base. Therefore, without resetting the charge_ctl bit, when the pump is connected to the charge base, voltage will be presented to the components of the pump, which could cause damage to the components. Therefore, in order to prevent the damage to the components of the pump, the bit charge_ctl is cleared. The bit slope_2 is simply reset for the next time that it is used in steps 246-250 and 252 as will be described hereafter.

If, at step 224, bit ok_to_charge is set indicating that the pump is connected to the charger base, the program passes to step 240. Steps 240-246 in FIG. 4F$ii$ monitor the voltage of the batteries. NiCad batteries exhibit a rise in cell voltage while charging. Once they have reached full capacity, the voltage stabilizes. Continuing charging above a minimum charge to offset the batteries inherent self-discharge results in a decreasing cell voltage. This decreasing cell voltage is sensed here by detecting the voltage peak of $V_B$ and a subsequent decreasing voltage. When the software detects that the voltage of $V_B$ has decreased after a voltage peak determined by byte $v_{13}$ peak by a magnitude of 60 mV, quick charging will be terminated. This method has the additional advantage of minimizing the amount of energy dissipated by the batteries as heat. This maximizes the overall cell life and the charge acceptance of the cell.

At step 240, register charge_timer is tested to determine if sufficient time has elapsed while measuring the battery voltage $V_B$ for the voltage to have stabilized. If register charge_timer has recorded less than or equal to two minutes of quick charge, the program passes to step 230. If register charge_timer has recorded more than two minutes of quick charge, the software assumes that the battery voltage has stabilized or started a positive trend after being connected to the charge base and receiving quick charge. Consequently, the program passes to step 242.

Steps 242-250 in FIG. 4Fii find the peak and the slope of the battery voltage $V_B$ when receiving a quick charge. This information is used to determine when a battery has been charged to full capacity. Step 242 compares the voltage stored in byte v_peak to $V_B$. If the voltage in byte v_peak is less than $V_B$, then the battery voltage is rising. In this case, the program passes to step 244, where v_peak is set equal to $V_B$. If v_peak is greater than or equal to $V_B$, the program passes directly to step 246 without changing the value in byte v_peak.

Figure 7:
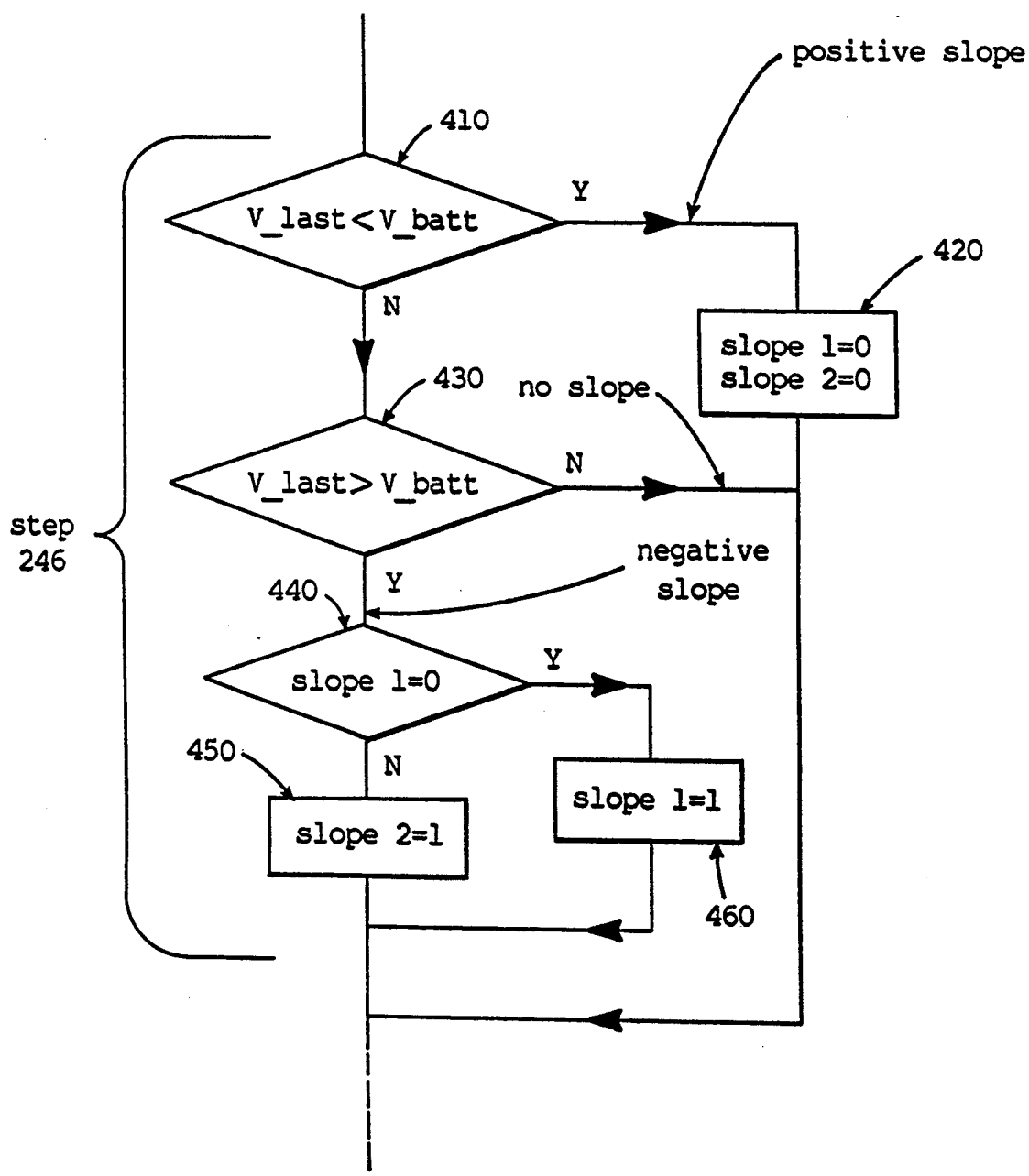
FIG. 7 is a flow chart of a part of the software shown in FIGS. 4a–4gii.

Step 246 tests for a decreasing with respect to time. This is done by comparing the current battery voltage to prior measured battery voltages to see if the battery voltages are increasing or decreasing in time. The software workings of this step are shown in more detail in FIG. 7. Step 246 is entered via step 410.

At step 410 the value stored in register $v_{13}$last, which is the value of the battery voltage measured on the immediate prior pass through the software, is compared to the current measured battery voltage stored in register v_batt. If the value of register v_last is smaller than the value stored in register v_batt, the battery voltage is increasing. In this case, the program passes to stop 420. At step 420, bits slope_1 and slope_2 are cleared which indicates a "positive" slope for the measured battery voltage $V_B$. From step 420, the program passes directly to step 230.

If, at step 410, the value of register v_last is greater than or equal to the value in register v_batt, the slope of the measured battery voltages is either decreasing or staying the same, so the program passes to step 430.

Step 430, in combination with step 410, determines whether the value of register v_last is equal to the value of register v_batt. In order to get to step 430, the value of register v_last has already been found to be greater than or equal to the value of register v_batt at step 410. Step 430 then evaluates whether the value of register v_last is larger than the value in register v_batt. If it is, this indicates that the slope of the measured battery voltages is decreasing so the program passes to step 440. If the value of register v_last is not larger than the value in register v_batt, this indicates that the slope of the measured battery voltages is staying the same so the program passes directly to step 230.

Step 440 determines whether bit slope_1 has already been set on a previous pass through the software. If bit slope_1 has already been set, this indicates that the software has already determined on a previous pass through the software that the measured battery voltages have been decreasing. As a result, the program passes from step 440 to step 450 where bit slope_2 is set. Both bits slope_1 and slope_2 being set indicates to the subsequent software that the measured battery voltages are decreasing.

If bit slope_1 is not set at step 440, the software has not already determined on a previous pass through the software that the measured battery voltages have been decreasing. As a result, the program passes from step 440 to step 460. At step 460, because the software has already determined in steps 410 and 430 that the measured battery voltages are just starting to decrease, bit slope_1 is set. Bit slope_1 being set without also having bit slope_2 being set indicates that the measured battery voltages have just started to decrease. From both steps 450 and 460, the program passes to step 230.

Step 230 in FIG. 4Fiii test register charge_timer for a 6 hour timeout for quick charging. If this timeous has been reached, the program passes to step 234 where the quick charge cycle is terminated by clearing bit quick_charge_req regardless of the value stored in byte v_peak and whether $V_B$ is still increasing. Bit quick_charge_req is cleared because the batteries are fully charged and no further quick charging is needed. This prevents severe overcharging in the event that the batteries did not exhibit the typical voltage peak during charging.

Step 234 also clears bit charge_ctl so that quick charging is stopped and trickle charge will be sent to the batteries. The wait_timer register is reset to zero to begin timing the 2 hours until another quick charge. Bit charge_wait is set since the pump is now in the 2 hour period before the next quick charge can be initiated. Finally, step 234 sets register charge_timer to 6 hours in case step 234 was reached through steps 252 and 254. The program then passes to step 236.

If at step 230, register charge_timer has not reached its 6 hour timeout so that its value will be less than or equal to 6 hours, the program passes to step 231. Step 231 compares the current value of $V_B$ to the value of 4.88 v. If $V_B$ is greater than 4.88 v, indicating that the batteries may be bad or that the batteries are not exhibiting their typical peak charged voltage because they are being charged at cold ambient temperatures, the program passes to step 234 where the operations of step 234 are described above are carried out. If at step 231, $V_B$ is less than or equal to 4.88 v, the program passes to step 252.

Step 252 looks at the value of bit slope_2 to see if it is set thereby indicating that the slope of the measured battery voltage is negative. If bit slope_2 is not set, the program passes to step 232 where bit charge_ctl is set thereby enabling quick charge. If at step 252, bit slope_2 is set, thereby indicating that the slope of the measured battery voltages is negative, the program passes to step 254.

At step 254, the difference between the peak voltage stored in byte v_peak and the current battery voltage $V_B$ is compared to a preset value, v_diff, which in the preferred embodiment is 60 mv. If the difference between v_peak and $V_B$ is greater than v_diff, the slope of the measured voltages is negative and the voltage difference between the peak voltage measured and the current voltage exceeds the preset limit. This indicates that the NiCad batteries have been charged to their maximum capacity so the program passes to step 234 where the quick charge is terminated as described above. If the difference between v_peak and $V_B$ does not exceed the threshold value set by v_diff, the program passes to step 232 to initiate quick charging by setting bit charge_ctl. Steps 232 and 234 both pass to step 236.

To summarize, quick charge is terminated either by quick charging for six hours or by the battery voltage rising to a peak and then falling past a preset voltage difference threshold.

If bit charge_wait is set in step 200 the microprocessor is still waiting for 2 hours to elapse since the end of the previous quick charge and the program passes to step 202. At step 202, the microprocessor again assures that no quick charge will be delivered by clearing bit charge_ct1. The program then passes to step 204 where register wait_timer is examined to see if its value is greater than or equal to 2 hours. If it is, the program passes to step 208 where the value of register charge_timer is evaluated to see if it contains a value less than 6 hours, indicating that the batteries can receive additional charge. If the batteries are already fully charged, as indicated by register charge_timer having a value of 6 hours, there is no need for additional quick charging. Therefore, the program passes from step 208 to step 236.

If, at step 208, register charge_timer has a value less than 6 hours, additional quick charging can be done to the batteries so the program passes from step 208 to step 210. At step 210, the bit quick_charge_req is set so that quick charging will be enabled. Also at step 210, the bit charge_wait is rest to zero so that quick charging can be initiated. In addition, the register wait_timer is reset to zero since quick charge is being requested so there can not yet be a completed full 6 hour quick charging cycle. Byte charge$_{13}$timer is cleared to re-enable a quick charge for a maximum 6 hours in length. Register v_peak and bits slope$_{13}$ 1 and slope$_{13}$ 2 are reset to begin the detection of a drop in battery voltage when the battery cells reach full capacity during quick charging. From step 210, the program passes to step 236.

Returning to step 204, if the value of register wait_timer is less than 2 hours, indicating that it has been less than 2 hours since the completion of a 6 hour quick charge cycle, the program passes to step 206 where the register wait_timer will be incremented. In passing through step 206, incrementing register wait_timer causes wait_timer to act like a timer. From step 206, the program passes to step 236.

FIG. 4G$i$ and 4G$ii$ briefly describe the operation of the error handling software as related to battery conditions. This software runs concurrently with the software described in steps 110 to 236. This error handling software begins at step 299 which is initiated when the program runs for the first time. At step 299, bit err_bits is set equal to zero. From step 299 the program passes to step 302 where, because bit err_bits is equal to zero, the program passes through 334 and then to step 300.

At step 300, bit abort_op is continuously monitored to detect any error conditions. Bit abort_op is set when an error condition is found. If no error is detected, the program cycles from step 300 through step 334, which handles non-battery related errors, back to step 300. Setting bit abort_op immediately results in cancellation of the current operation of the pump and begins execution of the error handler. If bit abort_op is set this indicates that an error condition is present and the program passes to step 302.

At step 302, the register err_bits is examined for an error condition indicating that the abort_op bit has been set by a low battery, dead battery, or bad battery condition. The register err_bits is a bit array storing error-indicating bits for operating errors. The bits are set by the bit registers mentioned above. If not bits are set, this indicates that step 302 was entered from step 299 as a result of starting the program. In this case, normal execution continues by passing the program back to step 300 through step 334 so that a monitoring loop is made.

If an error bit is set in register err_bits, the program passes to step 304 where bit abort_op is cleared so that any new error conditions will be detected while this part of the program is running. The program then passes from step 304 to step 306 where the bit bad_$_{pl}$ batt_flag is tested for a bad battery condition. If this bit is set, indicating that the batteries are bad, the program passes to step 308 where the highest priority bad battery error message is displayed. In the preferred embodiment, this error message is all segments of the LED display flashing for 10 seconds as an error indicator. Thereafter, step 308 directs the microprocessor to shut of fall power to the pump circuits thereby turning off the pump.

If, at step 306, there is no bad battery condition so that bit bad_batt_flag is not set, the program passes to steps 310 and 312 where the dead_batt_flag and low_batt_flag bits are tested respectively. If, at step 310, bit dead_batt_flag is set, indicating a dead battery, the program passes to step 314 for initiation of an alarm. If the dead_batt_flag is not set, thereby indicating that there is not a dead battery condition, the program passes to step 312 where the low_batt_flag bit is tested. If this bit is set, thereby indicating a low battery condition, the program passes from step 312 to step 341. If, at step 312, no low battery condition is indicated, the program then passes from step 312 through step 334 back to step 300.

The purpose of steps 306, 310 and 312 is to determine whether the source of the error that set register abort_op is battery related. If none of the bad_batt_flag, dead_batt_flag or low_batt_flag bits are set, some other non-battery related error has caused register abort_op to be set. Consequently, the program passes back to step 300 through step 334 so that these other error conditions can be appropriately dealt with.

The LOW BATT error display loop is entered at step 314. At step 314, bits charge_req_ack and in_lb_loop are set to prevent generation of further LOW BATT messages. The program then passes to step 316 where the microprocessor tests register err_status. If register err_status has a value less than or equal to 2, this indicates that the error condition is a low battery condition as opposed to a dead battery condition as previously determined in steps 155-170. As a result, the program passes to step 318 where register err_status is set with the value "2", which will cause the "LOW BATT " display to be displayed at step 326, and the audible alarm is turned on at low volume.

At step 316, a value in register err$_{13}$status of three or greater results in a full-volume audible alarm initiated by step 158 by calling the alarm generator with a "full volume" argument and negates the ability to acknowledge the alarm with the START/HOLD key by the err_status _byte being read by the keyboard driver; acknowledgement is only allowed with the charge base. In this case, the program passes to step 320. From step 318, the program passes to step 320.

If, at step 316, the value of register err_status is not less than 3, this indicates that the program is in the midst of a bad battery condition as initiated by step 158. Therefore, since the bad battery status is a priority message, there is not need to pass to step 318 for indicating a lower priority dead battery or low battery message. Consequently, if the program is currently in a bad battery error message display loop, the program passes from step 316 directly to step 320.

At step 320, the bit abort_op is tested to see if another error has occurred in the time between when register abort_op was cleared at step 304 and the execution of step 320. If another error has occurred, bit abort_op will now be set. In this case, the program passes from step 320 to step 328.

AT step 328, the status of bit abort_op is again tested. If it is set, indicating that step 328 was entered from step 320 thereby indicating a new error condition has been detected, the program passes to step 330 where bit charge_req_ack is cleared so that the error handler will return to the LOW BATT display after the higher priority error is acknowledged by the pump user. From step 330, the program passes to step 332.

If at step 320, bit abort_op is not set, thereby indicating that no new error condition has occurred in the current operation of the program, the program passes to step 322. At step 322, the microprocessor tests for the presence of the charge base via of bit of bit ok_to_charge. If the pump is connected to the charge, this bit will be set so step 322 is exited to step 328 so that the LOW BATT message will not be ultimately displayed. Instead, because the batteries are low and no new error condition exists and because the charger is connected to the pump, the batteries will be charged.

In this case, upon entering step 328, bit abort_op will not be set so that the program exits step 328 and passes directly to step 332. At step 332, bit in_b_loop is reset to zero so that upon detection of a new low battery error message, the loop may be initiated by passing from step 300 to steps 302 through 332.

If, at step 322, the pump is not connected to the charger so that bit ok_to_charge is not set, the program passes from step 322 to step 324. At step 324, the value of register err_status is tested. If the value of err_status is equal to zero, the error condition is fully acknowledged, so the program passes from step 324 through steps 328 to 332. If, however, the value of err_status is greater than zero, this indicates the presence of a battery error condition. Consequently, the program passes to step 326 where the low battery display is displayed on the display of the pump. From step 326, the program passes back to step 320 where a loop is formed. In order to get out of this loop, either a new error condition must be found so that bit abort_op will be set or the pump must be connected to the charger or the value of err_status must be reset to zero by pressing the START-/HOLD key twice.

Connecting the pump to the charger base at any time during the LOW BATT display will acknowledged that alarm condition and cancel the LOW BATT display because the ok_to_charge bit will be set which will be detected by the program as it passes through steps 300 through 332. The LOW BATT alarm may also be acknowledged with two presses of the START/HOLD key if the LOW BATT display is caused simply by a LOW BATT condition. Pressing the START/HOLD key in this condition will cause register err_status to be cleared which will in turn be recognized as the program passes through steps 300 through 332. The keypad driver recognizes the START/HOLD key in an error state, and will appropriately decrement the register err_status by additional software.

While the embodiment of the invention shown and described is fully capable of achieving the results desired, it is to be understood that this embodiment has been shown and described for purposes of illustration only and not for purposes of limitation. Further, it is to be understood that obvious changes and modifications to the description contained herein will occur to those skilled in the art which changes and modifications will still be within the scope of the invention.

We claim:

APPENDIX I

| | |
|---|---|
| abort_op | bit set when an operating error (including battery conditions) is detected. This bit forces the microprocessor to terminate all pumping operations and current displays and proceed to the error handler. |
| bad_batt_flag | bit set when battery voltage $V_B$ is outside limits of 2.6 and 4.9 volts. |
| batt15_timer | counter used to time the 15 minute LO BATT timeout, and to time the DEAD BATT and BAD BATT messages. |
| charge_ctl | bit set to control the charger base. When set, the charge base delivers quick charge (C/5). When clear, the charger base delivers trickle charge. |
| charge_req_ack | bit set when a LOW BATT is acknowledged by either placing the pump into the charger base or by pressing the START/HOLD key twice. |
| charge_timer | word counter that tracks the amount of quick charge time that has been delivered to the batteries. Range of 0 to 6 hours. |
| charge_wait | bit set when the microprocessor determines that it is in the 5 hour period between quick charge cycles. |
| dead_batt_flag | bit set when battery voltage is less than 3.20 volts. |
| err_bits | bit array storing error-indicating bits for operating errors. |
| err_status | byte that keeps track of the status of an error display. Normally set to 2 when an error is first generated. Decremented by pressing the START/HOLD key. Error messages are exited when err_status equals 0 (an alarm has been fully acknowledged). |
| in_bad_batt | bit set when the microprocessor is displaying the BAD BATT message. |
| in_bad_batt_loop | bit set when the microprocessor is displaying the BAD batt message. |
| in_low_batt | bit set when the microprocessor is displaying the DEAD BATT or LOW BATT messages. |
| in_low-batt_loop | bit set when the microprocessor is displaying the DEAD BATT or LOW BATT messages. |
| low_batt_flag | bit set when battery voltage is less than 3.56 volts. |
| motor_ctl | bit set when motor is to be turned on and rotating. |
| ok_to_charge | bit set when the pump is connected to an operating charge base. |
| quick_charge_req | bit set when the microprocessor requests C/5 charging for the battery. |
| shutdown | bit set when the microprocessor determines that no more execution is to take place. The timer-generated software detects this and terminates power to all circuitry and executes the STOP instruction. |
| slope_1 | bit set when trend of battery voltage $V_B$ vs. time is determined to have just begun to be negative ($dV_B/dt < 0$). |
| slope_2 | bit set when trend of battery voltage $V_B$ vs. time is determined to be negative ($dV_B/dt < 0$) and bit slope_1 has already been set. |
| turned_on | bit set when the pump is turned on; i.e., the display is on. The microprocessor is still active running the timers when turned_on is not set. |
| v_batt | byte storing the measured battery voltage $V_B$. |
| v_diff | the preset voltage difference between the peak voltage stored in register v_peak and the current voltage $V_B$ which, when the slope of the measured battery voltages is negative, indicates the NiCad batteries are fully charged. |
| v_last | byte storing the value of the battery |

-continued
APPENDIX I

| | |
|---|---|
| | voltage measured on the previous pass through the software. |
| v_peak | byte storing the peak voltage read by the A/D converter during the quick charge cycle - reset only at the beginning of a quick charge cycle. |
| wait_timer | word counter that tracks the amount of time elapsed after completion of a 6 hour quick charge cycle. Range of 0 to 5 hours. |

1. A device having a rechargeable electrical power source which may be attached to a base unit for charging said source, said unit having a charging circuit controllable to provide a high charging current and a low charging current, said device comprising:
   means for detecting the attachment of the device to the base unit; and
   means, responsive to said detecting means, for controlling said charging circuit to selectively provide said high or said low charging current including means for causing said charging circuit to provide said low charging current a first predetermined amount of time after starting to provide said high charging current and for preventing said charging circuit from providing said high charging current until a second predetermined time has elapsed after said first predetermined amount of time.

2. A device in accordance with claim 1 further comprising means for measuring the capacity of the power source.

3. A device in accordance with claim 2 wherein said detecting means detects the attachment of the device to the base unit by a change in said capacity of the power source.

4. A device in accordance with claim 1 wherein said controlling means further includes means for causing said charging circuit to provide said high charging current if the present capacity of the power source is below a predetermined level.

5. A device in accordance with claim 1 further comprising means for increasing said first predetermined amount of time if said detecting means detects said device is not attached to said base unit.

6. A device in accordance with claim 1 further comprising means for increasing said first predetermined amount of time an amount proportional to the energy that is drained from the power source while said device is not attached to said base.

7. A device in accordance with claim 1 wherein said high charging current is four times said low charging current.

8. A device in accordance with claim 6 wherein said high charging current is equal to the maximum current output of the power source divided by five.

9. A device in accordance with claim 1 further comprising:
   means, enabled when said charging circuit provides said high charging circuit to the power source, for measuring the voltage of the power source;
   means, connected to said means for measuring, for determining the peak voltage of the power source while receiving said high charging current;
   means for determining that the voltage of the power source has decreased a preset amount from the peak voltage measured of the power source and for thereafter directing said charging circuit to terminate providing high charging current to the power source.

10. In combination, a device having a rechargeable electrical power source and a base unit to which said device may be attached,
   said base unit including a charging circuit selectable between at least a first charging current and a second charging current, said currents being applied to the power source when said device and said base are attached, said device including detecting means having a first state when said device is attached to said base and a second state when said device is detached from said base.
   means, responsive to said detecting means, for selecting one of said charging currents when said detecting means is in said first state,
   first timer means for determining the amount of time said first charging current is applied to said source and for causing said selecting means to select said second charging current when the amount of time has reached a first predetermined value,
   second timer means for determining the amount of time since the amount of time determined by said first timer means reached said first predetermined value, and,
   means for preventing said selecting means from selecting said first charging current until the amount of time determined by said second timer means has reached a second predetermined value.

11. A device in accordance with claim 10 further comprising means for measuring the capacity of the power source.

12. A device in accordance with claim 11 wherein said detecting means detects the attachment of the device to the base unit by a change in the capacity of the power source.

13. A device in accordance with claim 10 wherein said selecting means further includes means for causing said charging circuit to provide a high charging current if the present capacity of the power source is below a predetermined level.

14. A device in accordance with claim 10 further comprising means for increasing said first predetermined amount of time if said detecting means detects said device is not attached to said base unit.

15. A device in accordance with claim 14 further comprising means of increasing said first predetermined amount of time an amount proportional to the energy that is drained from the power source while said device is not attached to said base.

16. A device in accordance with claim 10 further comprising:
   means, enabled when said charging circuit provided said high charging current to the power source, for measuring the voltage of the power source;
   means, connected to said means for measuring, for determining the peak voltage of the power source while receiving said high charging current;
   means for determining that the voltage of the power source has decreased a preset amount from the peak voltage measured of the power source and for thereafter directing said charging circuit to terminate providing high charging current to the power source.

17. The method of determining the charging of a rechargeable electrical power source in a device which may be attached to a base unit comprising a charging circuit, said method comprising the steps of:
- detecting the attachment of the device to the base unit in response to the attachment of the device to the base unit;
- enabling the charging circuit to provide a first charging current to the power source;
- timing the time the first charging current is provided to the power source; and causing the charging current to provide a low charging current of the power source after a first preselected period of time has elapsed; and
- preventing the charging circuit from again providing the first charging current after said first preselected period of time for a second preselected period of time.

18. A method in accordance with claim 17 further comprising the step of measuring the capacity of the power source.

19. A method in accordance with claim 17 wherein the attachment of the device to the base unit is detected by a change in said capacity of the power source.

20. A method in accordance with claim 18 further comprising the step of causing the charging circuit to provide said first charging current if the present capacity of the power source is below a predetermined level.

21. A method in accordance with claim 17 further comprising the step of increasing said first predetermined amount of time if said detecting means detects said device is not attached to said base unit.

22. A method in accordance with claim 21 further comprising means for increasing said first predetermined amount of time an amount proportional to the energy that is drained from the power source while said device is not attached to said base.

23. A method in accordance with claim 17 further comprising the steps of:
- measuring the voltage of the power source while said charging circuit provides said first charging current to the power source;
- determining the peak voltage of the power source while receiving said first charging current;
- determining that the voltage of the power source has decreased a preset amount from the peak voltage measured of the power source;
- directing, in response to a determination that the voltage of the power source has decreased a preset amount, said charging circuit to determine providing said first charging current to the power source.

24. In combination, a base unit and a plurality of devices each having a rechargeable electrical power source and which may be attached to said base for charging said source, said combination comprising:
- a charging circuit within said base unit controllable to provide a high charging current and a low charging current;
- each of said devices having means for detecting the attachment of each of said devices to said unit; and
- each of said devices being independent means, responsive to said detecting means for controlling said charging circuit, for selectively providing either said high or said low charging current, each of said controlling means controlling said circuit independently of other controlling means of other devices.

25. A combination in accordance with claim 24, wherein each of said controlling means includes means for causing said charging circuit to provide said low charging current to the corresponding device of said each of said controlling means a first predetermined amount of time after starting to provide said high charging current to said corresponding device and for preventing said charging circuit from providing said high charging current to said corresponding device until a second predetermined time has elapsed after said first predetermined amount of time.

26. A combination in accordance with claim 25 further comprising means for measuring the capacity of the power source.

27. A combination in accordance with claim 26 wherein said controlling means further includes means for causing said charging circuit to provide said high charging current if the present capacity of the power source is below a predetermined level.

28. A combination in accordance with claim 24 comprising means in each of said devices for increasing said first predetermined amount of time if said detecting means detects that respective said device is not attached to said base unit.

29. A combination in accordance with claim 28 further comprising means for increasing said first predetermined amount of time an amount proportional to the energy that is drained from the power source while respective said device is not attached to said base.

30. A combination in accordance with claim 24 further comprising:
- means, enabled when said charging circuit provides said high charging current to the power source, for measuring the voltage of the power source;
- means, connected to said means for measuring, for determining the peak voltage of the power source while receiving high charging current;
- means for determining that the voltage of the power source has decreased a preset amount from the peak voltage measured of the power source and for thereafter directing said charging circuit to terminate providing high charging current to the power source.

* * * * *

UNITED STATES PATENT AND TRADEMARK OFFICE
CERTIFICATE OF CORRECTION

PATENT NO. : 5,225,763
DATED : July 6, 1993
INVENTOR(S) : Krohn et al.

It is certified that error appears in the above-indentified patent and that said Letters Patent is hereby corrected as shown below:

In Col. 22, line 48, delete "of" and insert therefor -- for --.

In Col. 22, line 54, delete "provided" and insert therefor -- provides --.

In Col. 23, line 10, delete the first occurrence of "current" and insert therefor -- circuit --.

In Col. 23, line 10, delete "allow" and insert therefor -- a low --.

In Col. 23, line 10, delete "of" and insert therefor -- to --.

In Col. 23, line 50, delete "determine" and insert therefor -- terminate --.

In Col. 23, line 55, after "base" insert -- unit --.

In Col. 24, line 6, delete "being" and insert therefor -- having --.

Signed and Sealed this

Twenty-second Day of March, 1994

Attest:

BRUCE LEHMAN

*Attesting Officer*      *Commissioner of Patents and Trademarks*